US008906886B2

(12) United States Patent
Chen et al.

(10) Patent No.: US 8,906,886 B2
(45) Date of Patent: Dec. 9, 2014

(54) COMPOSITION AND METHOD FOR PROMOTING SURVIVAL OF AGED BASAL FOREBRAIN CHOLINERGIC NEURON LEADING TO PROVENTION AND TREATMENT OF AGE-RELATED NEURODEGENERATIVE DISORDER

(76) Inventors: Su Chen, San Antonio, TX (US); Rainbow Chen, San Antonio, TX (US)

( * ) Notice: Subject to any disclaimer, the term of this patent is extended or adjusted under 35 U.S.C. 154(b) by 1143 days.

(21) Appl. No.: 12/497,583

(22) Filed: Jul. 3, 2009

(65) Prior Publication Data

US 2011/0003775 A1    Jan. 6, 2011

(51) Int. Cl.
*A61K 31/661* (2006.01)
*A61K 31/683* (2006.01)
*A61K 31/685* (2006.01)

(52) U.S. Cl.
CPC ............ *A61K 31/683* (2013.01); *A61K 31/685* (2013.01)
USPC ............................................ 514/148; 514/78

(58) Field of Classification Search
USPC .................................................. 514/78, 148
See application file for complete search history.

(56) References Cited

U.S. PATENT DOCUMENTS

2008/0021000 A1 *   1/2008   Chen et al. ...................... 514/78

OTHER PUBLICATIONS

Fedorova—An n-3 Fatty Acid Deficiency Impairs Rat Spatial Learning in the Barnes Maze 2009 Behavioral Neuroscience vol. 123, No. 1.
Kim—Inhibition of Neuronal Paoptosis by Polyunsaturated Fatty Acids 2001 Journal of Molecular Neuroscience—vol. 16.
Auld—Nerve Growth Factor Rapidly Induces Prolonged Acetylcholine Release from Cultured Basal Forebrain Neurons: Differentiation between . . . May 15, 2001 Journal of Neuroscience.
Champeil-Potokar—Docosahexaenoic acid (22:6n-3) enrichment of membrane phospholids . . . European Journal of Neuroscience vol. 24 2006.
Farooqui—Biochemical Aspects of Neurodegeneration in Human Brain . . . Neurochemical Research, vol. 29, No. 11, Nov. 2004.
Favreliere—Age-Related changes in ethanolamine glycerophospholipid fatty acid . . . Neurobiology of Aging 21—2000.
Glomset—Role of Docosahexaenoic Acid in Neuronal Plasma Membranes Science's Stke Feb. 7, 2006.
Kim—Novel Metabolism of Docosahexaenoic Acid in Neural Cells Journal of Biological Chemistry Jun. 29, 2007 vol. 282, No. 26.
McGahon—Age-Related changes in synaptic function . . . Neuroscience vol. 94, No. 1—1999.
Salem—Mechanisms of Action in Docosahexaenoic Acid in the Nervous System—Lipids, vol. 36, No. 9—2001.
Sims—Presynaptic Cholinergic Dysfunction in Patients with Dementia Journal of Neurochemistry, 1983.
Terry—The Cholinergic Hypothesis of Age and Alzheimer's Disease-Related Cognitive Deficits . . . Journal of Pharmacology & Experimental Therapies 2003.
Mufson—Loss of Basal Forebrain P75NTR Immunoreactivity in Subjects with Mild Cognitive . . . Journal of Comparative Neurology vol. 443 2002.
Grutzendler—Cholinesterase Inhibitors for Alzheimer's Disease Drugs 2001: 61.
Kim—Substrate Preference in Phosphatidylserine Biosynthesis for Docosahexaenoic Acid Containing Species, Biochemistry 2004 vol. 43.
Kim—Effects of Docosapentaenoic Acid on Neuronal Apoptosis Lipids, vol. 38, No. 4—2003.
Lim—An extraordinary degree of structural specificity is required in neural phospholipids for optimal brain function . . . Journal of Neurochemestry 2005.
Guo—Neuronal Specific Increase of Phosphatidylserine by Docosahexaenoic Acid, J Mol Neurosci 2007.
Hamilton—n-3 Fatty Acid Deficiency Decreases Phosphatidylserine Accumulation Selectively in Neuronal Tissues, Lipids, vol. 35, No. 8 2000.
Kim—Biochemical and biological functions of docosahexaenoic acid in the nervous system: modulation by ethanol, Chemistry & Physics of Lipids, 2008.
Akbar, Kim—Neurobiology DHA Increases PS to promote Neuronal Survival, Sci. STKE, Aug. 9, 2005.
Kim—Inhibition of Neuronal Apoptosis by Docosahexaenoic Acid, Journal of Biological Chemistry, vol. 275, No. 45, Nov. 10, 2000.

(Continued)

*Primary Examiner* — Jennifer M Kim
(74) *Attorney, Agent, or Firm* — Michael A. Blake

(57) ABSTRACT

A method of treating a subject and preventing in a subject age-dependent basal forebrain cholinergic dysfunction related neurodegenerative disorders, comprising: administering a lipid composition comprising a therapeutically effective amount of highly enriched 1-acyl chains/2-docosahexaenoic acid containing molecular species of highly pure phospholipids to promote survival of aged basal forebrain cholinergic neurons, the phospholipids selected from the group consisting of phosphatidylserine, phosphatidylethanolamine, and phosphatidyl-monomethylethanolamine. A composition for treating a subject and preventing in a subject age-dependent basal forebrain cholinergic dysfunction related neurodegenerative disorders, the composition comprising: a lipid composition comprising: a therapeutically effective amount of highly enriched 1-acyl chains/2-docosahexaenoic acid containing molecular species of highly pure phospholipids to promote survival of aged basal forebrain cholinergic neurons, the phospholipids selected from the group consisting of phosphatidylserine, phosphatidylethanolamine, and phosphatidyl-monomethylethanolamine. A process for preparing a lipid composition comprising a therapeutically amount of natural source-based highly enriched 1-acyl chains/2-docosahexaenoic acid containing molecular species of highly pure phosphatidylserine to promote survival of aged basal forebrain cholinergic neurons; the process comprising: purifying a natural source-based phosphatidylcholine by silica chromatography; obtaining a related lysophosphatidylserine species by phospholipase A2 catalysis of transphosphatidylated natural source-based phosphatidylserine species; acylating the lysophosphatidylserine species with natural docosahexaenoic acid to form 1-acyl chains/2-docosahexaenoic acid containing phosphatidylserine species; and purifying the 1-acyl cgains/2-docosahexaenoic acid containing phosphatidylserine species by silica chromatography.

5 Claims, 13 Drawing Sheets

(56) References Cited

OTHER PUBLICATIONS

Spector—Plasma Free Fatty Acid and Lipoproteins as Sources of Ployunsaturated Fatty Acid for the Brain, Journal of Molecular Neuroscience, 2001.
Lagarde—Lysophosphatidylcholine as a Carrier of Docosahexaenoic Acid to Target Tissue, Fatty Acids & Lipids—New Findings, 2001, vol. 88.
Thies—Unsaturated Fatty Acids Esterified in 2-Acyl-1-Lysophosphatidylcholine . . . Journal of Neurochemistry, 1992.
Lagarde—Docosahexaenoic acid: Nutrient and precursor of bioactive lipids, Lipid Sci. Technol. 2008, 110.
Chen—Phospholipid and fatty acid specificity of endothelial lipase . . . Elsevier Journal, 2007.
Arendash—A Diet High in Omega-3 Fatty Acids Does Not Improve or Protect . . . Neuroscience 2007 vol. 149.
Freund—Omega-3 Fatty Acid Treatment in 174 patients iwth Mild to Moderate Alzheimer Disease . . . Arch Neurol/vol. 63, Oct. 2006.
Hossain—Docosahexaenoic Acid and Eicosapentaenoic acid-enriched phosphatidylcholine . . . Molecular and Cellular Biochemistry 2006.
Brenna—Linolenic acid supplementation and conversion to n-3 long-chain polyunsaturated fatty . . . Elsevier Journal 2009.
Igarashi—Docosahexaenoic acid synthesis from -linolenic acid by rat brain is unaffected by dietary n-3 PUFA deprivation, Journal of Lipid Research vol. 48 2007.
Hogyes—Neuroprotective effect of developmental docosahexaenoi8c acid supplement against excitotoxic brain damage . . . Neuroscience 119, 2003.
Amaducci—Phosphatidylseerine in the Treatment of Alzheimer's Disease . . . Psychopharmacology Bulletin, vol. 24, No. 1, 1988.
Crook—Effects of Phosphatidylserine in Alzheimer's Disease Psychopharmacology Bulletin, vol. 28, No. 1, 1992.
Crook—Effects of Phosphatidylserine in age-associated memory impairment, Neurology, May 1991.
Jorissen—Safety of Soy-derived Phosphatidylserine in Elderly People Nutritional Neuroscience, 2002, vol. 5.
Pepeu—A Review of Phosphatidylserine Pharmacological and clinical effects . . . Pharmacological Research, vol. 33, No. 2, 1996.
Chen—Comparison of molecular species of various transphosphatidylated phosphatidyleserine (PS) . . . Elsevier Journal, 2008.
Hosokawa—Conversion to Docosahexaenoic Acid-Containing Phosphatidylserine from Squid . . . J. Agric. Food Chem. 2000.
Testet—Nonenzymatic synthesis of glycerolipids catalyzed by imidazole Journal of Lipid Research, vol. 43, 2002.
Hosokawa—Preparation of Therapeutic Phospholipids through Porcine Pancreatic Phospholipase A2-Mediated Esterification . . . JAOCS, vol. 72 1995.
Morillo—Synthesis of 1,2-Diacyl-sn-Glycerophosphatidylserine from Egg Phosphatidylcholine . . . Lipids, vol. 31, No. 5, 1996.
Galli—Prolonged Retention of Doubly Labeled Phosphatidylcholine in Human Plasma and Erythrocytes . . . Lipids, vol. 27, No. 12 1992.
Lemaitre—Blood Compartmental Metabolism of docosahexaenoic acid (DHA) in humas after ingestion . . . Journal of Lipid Research, vol. 40, 1999.
Tijburg—Biosysthesis of Phosphatidylethanolamine via the CDP-Ethanolamine route . . . Biochemical & Biophysical Research, May 15, 1989.
Palatini—Pharmacokinetic characterization of phosphatidylserine liposomes in the rat, Journal of Pharmacology, 1991.
Delong—Molecular Distinction of Phosphatidylcholine Synthesis between the CDP-Choline Pathway . . . Journal of Biological Chemistry, vol. 274, No. 42, 1999.
Illingworth—The Uptake and metabolism of plasma lysophosphatidylcholine in vivo . . . Biochemistry Journal, 1972.
Kubo—Preferential Incorporation of Docosahexaenoic Acid into Nonphosphorus Lipids . . . American Society for Nutritional Sciences 2000.
Masuzawa—Selective acyl transfer in the reacylation of brain glycerophospholipids. Biochimica et Biophysica Elsevier 1989.
Merkyl—Metabolism of Glycerolipids the Journal of Biological Chemistry, vol. 238, No. 3, Mar. 1963.
Selinger—Synthesis of fatty acid anhydrides by reaction with dicyclohexylcarbodiimide, Journal of Lipid Research, vol. 7, 1966.
Singh—Modulation of the activity and arachidonic acid selectivity of group X secretory Phospholipase . . . Journal of Lipid Research, vol. 48, 2007.
Cho—Structure, Function, and reglation of Group V phospholipase A2 Biochimica et Biophysica, Elsevier, 2000.
O'Meara—Galanin regulates the postnatal survival of a subset of basal forebrain cholinergic neurons PNAS, Oct. 20, 2000, vol. 97, No. 21.
Casamenti, et al., Phosphatidylserine reverses the age-dependent decrease in coritcal acetylcholine release: a microdialysis study, Eur. J. Pharmacology (1991), vol. 194, 11-16, Elsevier Science Publishers.
Chen, et al., Comparison of molecular species of various transphosphatidylated phosphatidylserine (PS) with bovine cortex PS by mass spectrometry, Chem. Phys. Lipids (2008), vol. 152, p. 46.

* cited by examiner

COMPOSITION AND METHOD FOR PROMOTING SURVIVAL OF AGED BASAL FOREBRAIN CHOLINERGIC NEURON LEADING TO PROVENTION AND TREATMENT OF AGE-RELATED NEURODEGENERATIVE DISORDER

FIELD OF THE INVENTION

The present invention relates to a method of using highly enriched 1-acyl chains/2-docosahexaenoic acid (DHA)—containing molecular species of highly pure phosphatidylserine (PS) or highly enriched 1-acyl chains/2-docosahexaenoic acid (DHA)—containing molecular species of highly pure phosphatidylethanolamine; and/or highly enriched 1-acyl chains/2-docosahexaenoic acid (DHA)—containing molecular species of highly pure phosphatidylmonomethylethanolamine based brain DHA transporters; to promote survival of aged basal forebrain cholinergic neurons (BFCN) through reversing abnormal levels of striatal neural membrane DHA PS species which leads to the activity recovery of both the p75 neurotrophin receptor and choline acetyltransferase in the BFCN. This both prevents and treats age-dependent basal forebrain cholinergic dysfunction related neurodegenerative disorders.

BACKGROUND OF THE INVENTION

Docosahexaenoic acid (22:6n-3; DHA) is an abundant component in the brain phospholipids. It plays an important role in prenatal brain development and maintenance of normal brain function. The brain DHA deficiency can reduce normal levels of neural membrane DHA molecular species of phospholipids, leading to markedly influencing optimal learning and memory [Fedorova, et. al., An n-3 fatty acid deficiency impairs rat spatial learning in the Barnes maze, *Behav. Neurosci.*, 123, 196 (2009)] and causing neuronal apoptosis [Kim, et. al., Inhibition of neuronal apoptosis by polyunsaturated fatty acids, *J. Mol. Neurosci.* 16, 223 (2001)].

It has been demonstrated that the maintenance of normal levels of neural membrane DHA phosphatidylserine and DHA plasmalogen phosphatidylethanolamine species [Favrelere, et. al., Age-related changes in ethanolamine phospholipid fatty acid levels in rat frontal cortex and hippocampus, *Neurobiol. Aging* 21, 653 (2001); McGahon, et. al., Age-related changes in synaptic function: analysis of the effect of dietary supplementation with omega-3 fatty acids, *Neuroscience* 94, 305 (1999)] is essential for keeping normal membrane function [Glomset, Role of docosahexaenoic acid in neuronal plasma membrane. *Sci. STKE*, page 6, (2006); Salem et. al., Mechanisms of action of docosahexaenoic acid in the nervous system, *Lipids* 36, 945 (2001)]. Continuous supply of DHA into the brain and unique metabolism of DHA in relation to its incorporation into neural membrane phospholipids plays an important role in maintaining both neural membrane fluidity and gap junction coupling capacity, in order to keep normal expression of neurotrophin receptors and effective retrograde transport of the NGF-neurotrophin receptor complexes from cerebral cortex and hippocampus to basal forebrain [Kim, Novel metabolism of docosahexaenoic acid in neural cells, *J. Biol. Chem.* 282, 18661 (2007); Champeol-Potokar, et. al., Docosahexaenoic acid (22:6n-3) enrichment of membrane phospholipids increases gap junction coupling capacity in cultured astrocytes, *Euro. J. Neurosci.* 24, 3084 (2006); Farooqui, et, al., Biochemical aspects of neurodegeneration in human brain: involvement of neural membrane phospholipids and phospholipase $A_2$, *Neurochemical Res.* 29, 1961 (2004)] in order to inhibit neuronal apoptosis because an important neurotransmitter acetylcholine is synthesized mainly in basal forebrain cholinergic neurons [Terry and Buccafusco, The cholinergic hypothesis of age and Alzheimer's disease-related cognitive deficits: Recent challenges and their implications for novel drug development. *The Journal of Pharmacology and Experimental Therapeutics*, 306, 821 (2003); Auld, et. al., Nerve growth factor induces prolonged acetylcholine release from cultured basal forebrain neurons: differentiation between neuromodulatory and neurotrophinc influences, *J. Neurosci.* 21, 3375 (2001)]. It has been reported that acetylcholine synthesis, choline acetyltransferase activity and expression of p-75 neurotrophin receptor in patients with Alzheimer's disease have been found to be markedly reduced at least 40%, compared with controls [Sims, et. al., Presynaptic cholinergic dysfunction in patients with dementia, *J. Neurochem.* 40, 503 (2006); Mufson, et al., Loss of basal forebrain $P75^{NTR}$ immunoreactivity in subjects with mild cognitive impairment and Alzheimer's disease. *J. Comparative Neurology* 443, 136 (2002)].

The following scheme shows the pathway of biosynthesis and metabolism of an important neurotransmitter acetylcholine in neurons:

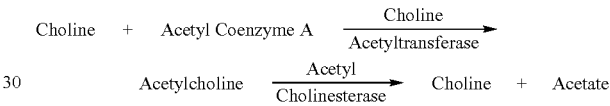

The mechanism of the current drugs for treatment of age-dependent cholinergic dysfunction related neurodegenerative disorders is to inhibit the activity of acetylcholinesterase, in order to decrease further degradation of acetylcholine in the brain [Grutzendler and Morris, Cholinesterase inhibitors for Alzheimer's disease, *Drugs* 61, 41 (2001)], rather than to promote neuronal survival. Because age-dependent neurodegenerative diseases are a progressive disorder, the cure becomes much more difficult or even impossible if the prevention and treatment start at a later stage of the diseases. However, an ideal drug used for such disorders should enable to both simultaneously delay or halt the underlying pathological process and improve memory and other clinical deficits.

The study further indicates that neuronal apoptosis under adverse conditions can be prevented by DHA enrichment in a phosphatidylserine (PS)—dependent manner, and depletion of DHA from neuronal tissues can influence biosynthesis and accumulation of PS [Kim, et. al., Substrate preference in phosphatidylserine biosynthesis for docosahexaenoic acid containing species, *Biochemistry*, 43, 1030 (2004)]. Furthermore, it is also important to point out that the provision of docosapentaenoic acid (22:5n-6; DPA) in place of DHA is sufficient neither for fully supporting PS accumulation nor for neuronal survival [Kim, et. al., Effects of docosahexaenoic acid on neuronal apoptosis, *Lipids* 38, 453 (2003); Lim et. al., An extraordinary degree of structural specificity is required in neural phospholipids for optimal brain function: n-6 docosapentaenoic acid substitution for docosahexaenoic acid leads to a loss in spatial task performance, *J. Neurochem.* 95, 848 (2007)].

It is clear that DHA positively modulates biosynthesis and accumulation of neural membrane DHA PS species, promoting neuronal survival. Rising the level of PS by DHA enrichment can be observed only in neural cells, representing a unique mechanism for expending DHA PS and PS pools in mammalian neurons, in order to inhibit neuronal apoptosis [Hamilton, et. al., n-3 fatty acid deficiency decreases phosphatidylserine accumulation selectively in neuronal tissues, *Lipids,* 35, 863 (2000); Guo, et. al., Neuronal specific increase of phosphatidylserine by docosahexaenoic acid, *J. Mol. Neurosci.* 33, 67 (2007)].

In summary, a DHA deficient diet can cause brain DHA deficiency, especially in aging adults. Effective supply of DHA to brain tissues in order to keep normal levels of DHA or to reverse abnormal levels of neural membrane DHA PS is of vital importance in the prevention and treatment of age-dependent neurodegenerative disorders [Kim, et. al., Inhibition of neuronal apoptosis by docosahexaenoic acid (22:6n-3). *J. Biol. Chem.* 275, 35215 (2000); Kim, Biochemical and biological functions of docosahexaenoic acid in the nervous system: modulation by ethanol, *Chem. Phys Lipids,* 153, 34 (2008); Editor's Choice, DHA Increases PS to Promote Neuronal Survival, *Sci. STKE,* 2005, p286 (2005)].

Because it cannot be synthesized in the brain, DHA has to be supplied entirely from the diet and is then delivered into the brain by plasma [Spector, Plasma free fatty acid and lipoproteins as sources of polyunsaturated fatty acids for the brain. *J. Mol. Neurosci.* 16, 159 (2001)]. Unlike other tissues, the brain uptake of DHA needs to overcome the blood-brain barrier (BBB). However, to further understand the mechanism by which DHA phospholipid carriers pass across the BBB is important in preparing mechanism-based DHA phospholipid transporters.

Generally, DHA can be delivered into the brain in forms of both non-esterified DHA and phospholipids. The DHA carried by lysophospholipids is preferred transporters to pass across the BBB [Chen and Subbaiah, Phospholipid and fatty acid specificity of endothelial lipase: potential role of the enzyme in the delivery of docosahexaenoic Acid (DHA) to tissues, *Biochim. Biophys. Acta,* 171, 1319 (2007); Lagarde et. al., Lysophosphatidylcholine as preferred carrier form of docosahexaenoic acid to the brain, *J. Mol. Neurosci.* 16, 201 (2001); Thies et. al., Unsaturated fatty acids esterified in 2-acyl-1-lysophosphatidylcholine bound to albumin are more efficiently taken up by the young rat brain than the non-esterified form, *J. Neurochem.* 59, 1110 (1992)] because the incorporation of DHA into the brain is approximately 10-fold higher from enzyme-catalyzed 2-DHA lysophospholipids than from non-esterified DHA at various times of analyses [Lagarde, Docosahexaenoic acid: Neutrient and precursor of bioactive lipids, *Eur. J. Lipid Sci. Technol.* 110, 673 (2008)].

For lipids based brain DHA transporters, use of a composition that consists of highly enriched DHA-containing lipid species is a must. Orally administered DHA triglyceride carriers, which are present in current supplements including fish, algae and krill oils, have shown benefits for the human health, but it is still questionable whether these lipid mixtures are qualified as effective DHA transporters in the delivery of DHA into the brain, especially aged brain [Arendash, et. al., A diet high in omega-3 fatty acids does not improve or protect cognitive performance in Alzheimer's transgenic mice, *Neuroscience,* 149: 286 (2007); Freund-Levi et al., co-3 fatty acid treatment in 174 patients with mild to moderate Alzheimer's disease: Omeg AD study, *Arch Neurol.* 63; 1402 (2006)]. Because DHA lipid species metabolite differently from others, it is hard to further understand pharmacological and nutritional functions of those DHA lipid species in a mixture form. [Hossain, et. al, Docosahexaenoic acid and eicosapentaenoic acid-enriched phosphatidylcholine liposomes enhance the permeability, transportation and uptake of phospholipids in Caco-2 cells. *Molecular and Cellular Biochemistry,* 285, 155 (2006); Chen and Subbaiah, Phospholipid and fatty acid specificity of endothelial lipase: potential role of the enzyme in the delivery of docosahexaenoic Acid (DHA) to tissues, *Biochim. Biophys. Acta,* 171, 1319 (2007)]. Although the ethyl DHA/EPA drug (over 80% purity) may alleviate coronary atherosclerosis, it may not be qualified as brain DHA transporters to overcome the blood-brain barrier (BBB).

On the other hand, the capacity of the brain to convert α-linolenic acid (18:3n-3; ALA) or eicosapentaenoic acid (20:5n-3; EPA) to DHA is limited [Igarashi et. al., Docosahexaenoic acid synthesis from alpha-linolenic acid by rat brain is unaffected by dietary n-3 PUFA deprivation, *J. Lipid Res.* 48: 1150 (2007)]. For example, converting ALA and EPA to DHA involves more than single desaturation and elongation step, and yields of the DHA formed by this route is very low [Brenna, et. al., alpha-Linolenic acid supplementation and conversion to n-3 long-chain polyunsaturated fatty acids in humans, *Prostaglandins Leukot. Essent. Fatty Acids,* 80, 85 (2009)]. Due to structural specificity of DHA for brain requirements, the study strongly suggests that a direct supply of DHA to the brain is required against neuronal apoptosis [Kim, et. al., Inhibition of neuronal apoptosis by docosahexaenoic acid (22:6n-3), *J. Biol. Chem.* 275, 35215 (2000)].

Because brain DHA deficiency can cause brain function disorders, particular during periods of brain development and aging, the methods of using various compositions of lipid nutrients and potential drugs have been applied for enhancing levels of DHA in the brain, in order to improve general brain function.

U.S. Pat. No. 5,869,530 discloses a method of using phospholipids as dietary supplements for improving general brain function. Mixtures of phospholipids including phosphatidylcholine and phosphatidylethanolamine are extracted from chicken egg yolk, but DHA molecular species obtained from this natural resource are absent.

U.S. Pat. No. 5,716,614 discloses a method of transporting DHA into the brain by EPA and DHA aminophospholipids-conjugated polycationic carriers (e.g. poly-lysine and poly-arginine or poly-ornithine) rather than highly pure DHA aminophospholipids, in order to improve function of mammalian brain.

Japanese patent 06256179 discloses the method for preparing 1,2-polyunsaturated fatty acids—3-phosphorycholine, or 3-phosphorylethanolmine, or 3-phosphorylserine, or 3-phosphorylinositol for improving learning ability and for treating senile dementia. However, Japanese patent 06256179 does not disclose highly enriched 1-acyl chains/2-DHA—containing molecular species of highly pure phospholipids for promoting survival of aged basal forebrain cholinergic dysfunction related neurodegenerative disorders.

Japanese 06279311 discloses the method of using a mixture of polyunsaturated fatty acids—containing phosphatidylserine species for treatment of senile dementia, especially Alzheimer's disease. However, the said compositions do not comprise a highly enriched 1-acyl chains/2-DHA—containing molecular species of highly pure phosphatidylserine, as well as highly pure phosphatidylethanolamine and highly pure phosphatidyl-monomethylethanolamine, for promoting survival of aged basal forebrain cholinergic neurons to prevent and treat age-related neurodegenerative diseases.

U.S. Pat. No. 6,964,969 discloses a method of treating impaired or deteriorating neurological function using a mixture of n-3/n-6 fatty acids and vitamins.

U.S. Pat. No. 5,668,117 discloses a method of treating age and Alzheimer's disease by administrating Vitamins. Similar effects for treatment of age and Alzheimer's disease using dehydroepiandrosterone has been also disclosed in U.S. Pat. No. 4,812,447.

WO patent 2007/073178 discloses a method of using compositions comprising DHA, proteins and manganese for improving membrane composition.

WO patent 1997/39759 discloses the methods for the preparation of 1,2-DHA-containing phosphatidylcholine species for the treatment of bipolar disorders. However, said compositions do not comprise highly enriched 2-DHA—containing molecular species of highly pure phosphatidylserine, or highly pure phosphatidylethanolamine or/and highly pure phosphatidyl-monomethylethanolamine.

WO patent 2005/051091 discloses a method of developing cognitive and vision functions of infants and children using a mixture of glycerophospholipid in combination with sphingomyelin or cholesterol.

Other published patents also documented methods of using mixtures of phospholipids, sphingomyelins and n-3 and n-6 fatty acids for the treatment of (1) a wide range of diseases [EP patent 1279400], (2) multiple traumata, burns, infections, and chronic inflammatory disease [EP patent 0311091], (3) hepatic cirrhosis and diarrhea, and (4) cancer diseases [EP patent 1426053].

From above published results, it is clear to see that the prior art does not disclose using highly pure 1-acyl chains/2-DHA aminophospholipids for promoting survival of aged basal forebrain cholinergic neurons.

The research paper and university study also reported the methods of using polyunsaturated fatty acids, such as DHA against excitotoxic brain damage of infant rats [Hogyer, et. al., Neuroprotective effect of developmental docosahexaenoic acid supplement against excitotoxic brain damage in infant rats, Neuroscience, 119, 999 (2003)]. The positive effect of long-chain polyunsaturated fatty acids on brain function in newborn and aged rats has been shown as well. But the methods of using highly pure 1-acyl chains/2-DHA aminophospholipids to promote survival of basal forebrain cholinergic neurons have not been claimed in the studies.

U.S. Pat. No. 5,654,290 discloses the methods of using polyunsaturated fatty acids based drugs, which include highly pure 2-DHA triglycerides, highly pure 1-short acyl chains/2-DHA PC species, and highly pure 2-DHA lysoPC species, to treat brain disorders. However, highly pure 1-acyl chains/2-DHA PE, highly pure 1-acyl chains/2-DHA PMME and highly pure 1-acyl chains/2-DHA PS are not disclosed in U.S. Pat. No. 5,654,290. Further, the patent does not disclose inhibiting neuronal apoptosis or treating basal forebrain cholinergic dysfunction related neurodegenerative disorders.

A method of using 1-acyl chains/2-DHA phosphatidylserine (PS) species, which is extracted from bovine cortex, as the first DHA phospholipid based drug in Europe to alleviate and treat Alzheimer's disease has been documented [Amaducci, et al., Phosphatidylserine in the treatment of Alzheimer's disease: Results of a multicenter study. *Psychopharmacology Bulletin* 24, 130 (1988); Crook, et al., Effect of phosphatidylserine in age-associated memory impairment. *Neurology*, 41, 644 (1991); Effect of phosphatidylserine in Alzheimer's disease, *Psychopharmacol. Bulletin* 28, 61 (1992); Pepeu, et al., A review of phosphatidylserine pharmaceutical and clinical effects: Is phosphatidylserine a drug for aging brain? *Pharmacology Research*, 33, 51 (1996)]. Although the purity of the bovine PS drug was over 80%, the percentage of DHA molecular species in the PS drug was about 10% [Chen and Li, Comparison of molecular species of various transphosphatidylated soy-phosphatidylserine with bovine cortex PS by mass spectrometry. *Chem. Phys. Lipids*, 152, 46 (2008)]. Based on previously used clinical dosage of bovine cortex PS drug (100-600 mg/day), it took at least 60 days to meet the expected effects because the actual amount of the 2-DHA species intake was in the range of 10-60 mg/daily only. The safety of oral administration of phospholipids including PS up to 600 mg/daily has been confirmed [Jorissen, et. al., Safety of soy-derived phosphatidylserine in elderly people, *Nutritional Neurosci.*, 5, 337 (2002)].

However, the risk of bovine spongiform encephalopathy (Mad Cow Disease) made use of the PS, the first DHA phospholipid based drug, potentially unsafe. Although methods of using alternatives of DHA PS species mixtures, made by transphosphatidylation of squid skin PC [Hosokawa, et. al., Conversion to docosahexaenoic acid-containing phosphatidylserine from squid skin lecithin by phospholipase D-mediated transphosphatidylation. *J. Agric. Food. Chem.* 48, 4550 (2000)] and fish liver PC [Chen and Li, Comparison of molecular species of various transphosphatidylated soy-phosphatidylserine with bovine cortex PS by mass spectrometry. *Chem. Phys. Lipids*, 152, 46 (2008)] to improve learning ability of DHA deficient mice have been reported[http://www.issfal.org.uk/index.php?option=com_content&task=view&id=55&Itemid=8 7%20#CS6], the maximal percentage of DHA species in the alternatives is approximately 45-55%. The method of using highly enriched 1-acyl chains/2-DHA molecular species (over 70% in the species mixture) of highly pure phosphatidylserine, highly pure phosphatidylethanolamine and highly pure phosphatidyl-monoethanolamine (more than 90% purity) for the purpose has never been reported.

For the preparation of natural source-based highly enriched 1-acyl chains/2-DHA-containing molecular species of highly pure phosphatidylserine (PS), the transphosphatidylation of highly enriched 1-acyl chain/2-DHA—containing molecular species of phosphatidylcholine [Hosokawa, et. al., Preparation of therapeutic phospholipids through porcine pancreatic phospholipase A2-mediated esterification and lipozyme-mediated acidolysis. *J. Am. Oil Chemist Soc.* 72, 1287 (1995)] can be used; an approach using nonenzymatic synthesis of phospholipids including phosphatidylserine in the presence of DHA-CoA has been described as well [Testet, et. al., Nonenzymatic synthesis of glycerolipids catalyzed by imidazole, *J. Lipid Res.* 43, 1150 (2002)]. However, these methods are expensive for large scale and/or industrial preparation.

The process for chemically synthesizing highly enriched 1,2-diDHA—containing molecular species of phosphatidylserine (PS) has been reported [Morillo, et., al., Synthesis of 1,2-diacyl-sn-glycerolphosphatidylserine from egg phosphatidylcholine by phosphoramidite methodology, *Lipids* 31, 541 (1996)]]. However, the safety of chemically synthesized diDHA PS has been not documented and therefore questioned. The pharmacological effect of diDHA PS species has never been reported as well.

SUMMARY OF THE INVENTION

The disclosed invention relates to a method of treating a subject and preventing in a subject age-dependent basal forebrain cholinergic dysfunction related neurodegenerative disorders, comprising: administering a lipid composition comprising a therapeutically effective amount of highly enriched 1-acyl chains/2-docosahexaenoic acid containing molecular species of highly pure phospholipids to promote survival of aged basal forebrain cholinergic neurons, the phospholipids selected from the group consisting of phosphatidylserine, phosphatidylethanolamine, and phosphatidyl-monomethylethanolamine.

The invention also relates to a composition for treating a subject and preventing in a subject age-dependent basal forebrain cholinergic dysfunction related neurodegenerative disorders, the composition comprising: a lipid composition comprising: a therapeutically effective amount of highly enriched 1-acyl chains/2-docosahexaenoic acid containing molecular species of highly pure phospholipids to promote survival of aged basal forebrain cholinergic neurons, the phospholipids selected from the group consisting of phosphatidylserine, phosphatidylethanolamine, and phosphatidyl-monomethylethanolamine.

In addition, the invention relates to a process for preparing a lipid composition comprising a therapeutically amount of natural source-based highly enriched 1-acyl chains/2-docosahexaenoic acid containing molecular species of highly pure phosphatidylserine to promote survival of aged basal forebrain cholinergic neurons; the process comprising: purifying a natural source-based phosphatidylcholine by silica chromatography; obtaining a related lysophosphatidylserine species by phospholipase A2 catalysis of transphosphatidylated natural source-based phosphatidylserine species; acylating the lysophosphatidylserine species with natural docosahexaenoic acid to form 1-acyl chains/2-docosahexaenoic acid containing phosphatidylserine species; and purifying the 1-acyl cgains/2-docosahexaenoic acid containing phosphatidylserine species by silica chromatography

BRIEF DESCRIPTION OF THE DRAWINGS

In FIG. 1A, peaks at m/z 452, 474,476,478 and 480 correspond to 16:0, 18:3, 18:2, 18:1 and 18:0 lysoPE species; in FIG. 1B, ions at m/z 762, 784, 786, 788 and 790 relate to 16:0/DHA, 18:3/DHA, 18:2/DHA, 18:1/DHA and 18:0/DHA PE species, made by the acylation of soybean based lysoPE species with DHA.

In FIG. 2A, peaks at m/z 466, 492 and 494 correspond to 16:0, 18:1 and 18:0 lysoPMME species; in FIG. 2B, ions at m/z 776, 802 and 804 relate to 16:0/DHA, 18:1/DHA and 18:0/DHA PMME species, made by acylation of the lysoPMME precursors with DHA.

In FIG. 3A, peaks at m/z 496, 518, 520, 522 and 524 correspond to 16:0, 18:3, 18:2, 18:1 and 18:0 lysoPS species; in FIG. 3B, ions at m/z 806, 828, 830, 832 and 834 relate to 16:0/DHA, 18:2/DHA, 18:2/DHA, 18:1/DHA and 18:0/DHA PS species, made by acylation of the lysoPS species with DHA.

in FIG. 4A, peaks at m/z 762 and 790 correspond to 16:0/DHA and 18:0/DHA PE species; in FIG. 4B, there is no lysoPE species presence after PE incubation without the phospholipase $A_2$; and in FIG. 4C, ions at m/z 452 and 480 are due to 16:0 and 18:0 lysoPE species that are only present after PE incubation with the enzyme.

in FIG. 4A, peaks at m/z 752, 776, 780 and 804 correspond to 16:0/20:5, 16:0/DHA, 18:0/20:4 and 18:0/DHA PMME species; in FIG. 4B, there is no ions due to lysoPMME species before the PMME incubation with the phospholipase $A_2$; and in FIG. 4C, ions at m/z 466 and 494 are due to 16:0 and 18:0 lysoPMME species that are present only after the PMME incubation with the enzyme.

In FIG. 6A, peaks at m/z 762 and 790 correspond to 16:0/DHA (24%) and 18:0/DHA PE (10%) species; after incubation of the PE with the GroupV (B) and the Group X (C) enzymes, relative intensities of ions at m/z 762 (16:0/DHA) and 790 (18:0/DHA) are much lower (percentages of 16:0/DHA PE down to 16% (for Group V) and 15% (for Group X), respectively; and 18:0/DHA PE down to 8% (for Group V) and 7% (for Group X), respectively, compared with those from the control sample (A). The results suggest that 16:0/DHA PE and 18:0/DHA PE species are effectively hydrolyzed by the Group V and the Group X enzymes, after the 30-min incubation, to form related lysoPE species.

DETAILED DESCRIPTION OF THE INVENTION

Figure 1:
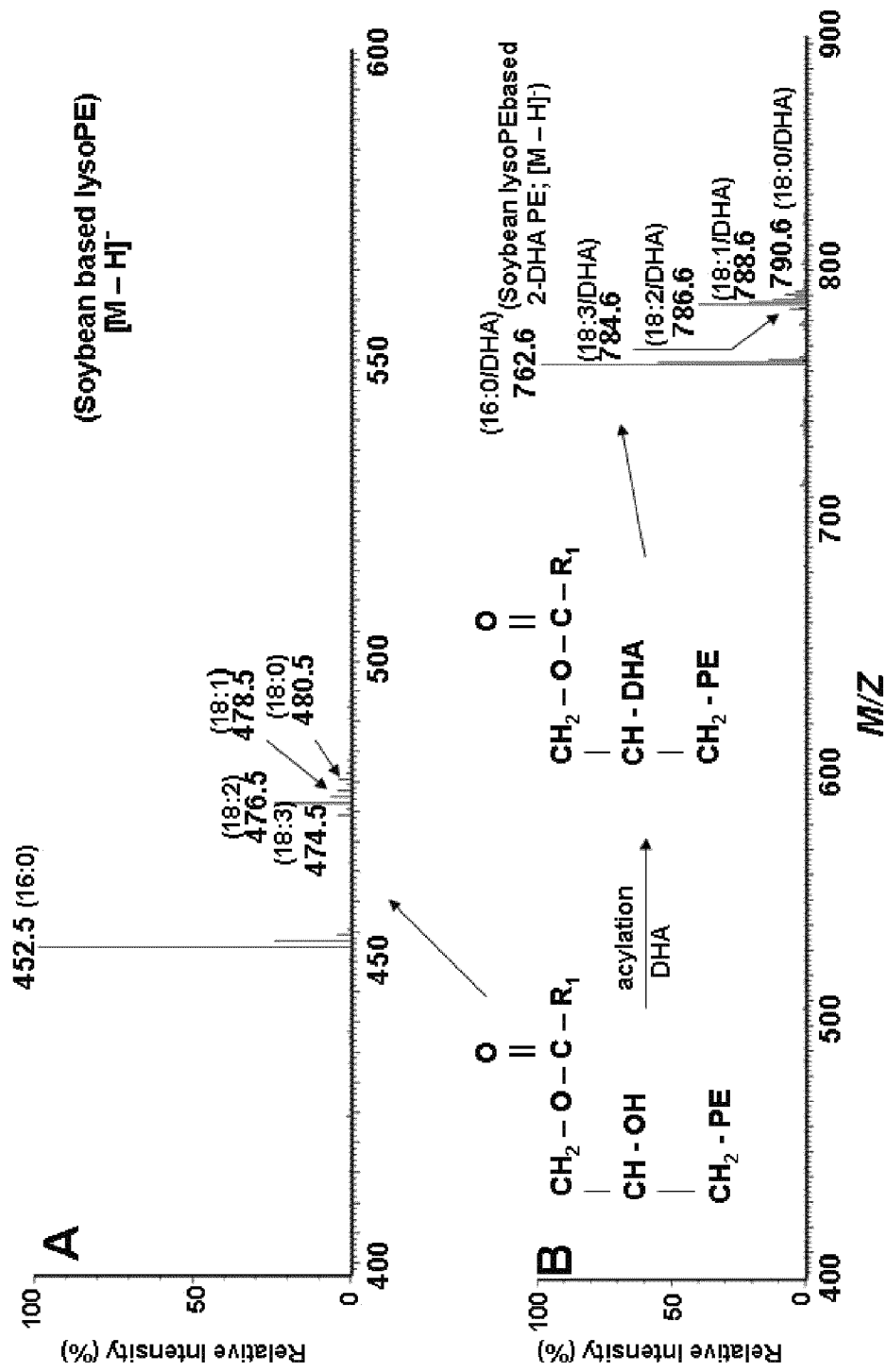
FIG. 1 shows the negative-ion electrospray mass spectra of (A) soybean based lysoPE species, and (B) 2-DHA PE, made from the soybean based lysoPE precursors.

Background of In Vivo and In Vitro Metabolic Fates of Phospholipids

It is an object of the present invention: to discover the methods of using highly enriched 1-acyl chains/2-docosahexaeoic acid—containing molecular species (over 70% in the species mixture) of highly pure aminophospholipids (over 90%), including phosphatidylserine, phosphatidylethanolamine and phosphatidyl-monomethylethanolamine, based transporters, to supply DHA into aged striatum for promoting survival of basal forebrain cholinergic neurons, in order to prevent and treat age-dependent basal forebrain cholinergic dysfunction and related neurodegenerative disorders. It must be stated here that the lipid composition used is not a mixture of lipids including non-DHA species—containing phospholipids and DHA species—containing triglycerides or phospholipids that contain less than 50% of DHA phospholipid species, so called "conjugated phospholipid DHA mixtures".

Use of the therapeutic reagents that contain highly pure DHA phospholipid species can significantly improve the pharmacological effects in prevention and treatment of aged-dependent neurodegenerative disorders.

Studies described fates of orally administered phospholipids, indicating that deacylation/reacylation circle in vivo is a major metabolic pathway [Galli et, al., Prolonged retention of doubly labeled phosphatidylcholine in human plasma and erythrocytes after oral administration. Lipids 27; 1005 (1992); Lemaitre-Delaunay et. al., Blood compartmental metabolism of docosahexaenoic acid (DHA) in humans after ingestion of a single dose of [$^{13}$C] DHA in phosphatidylcholine. J. Lipid Res. 40, 1867 (1999)]. For example, most of ingested 1-acyl chains/2-DHA phosphatidylcholine (2-DHA PC) can pass across intestinal barrier with limited degradation [Hossain, et. al, Docosahexaenoic acid and eicosapentaenoic acid-enriched phosphatidylcholine liposomes enhance the permeability, transportation and uptake of phospholipids in Caco-2 cells. Molecular and Cellular Biochemistry, 285, 155 (2006)]. However, a part of the lipids may be hydrolyzed by pancreatic phospholipase $A_2$ in small intestine [Arnesjo et al., Intestinal digestion and absorption of cholesterol and lecithin in the human, J. Gastroenterol. 4:653 (1969)], to form lysoPC and free DHA. After absorption, it is expected that lysoPC may be reacylated with the DHA by acyltransferase to reform newly-made 2-DHA PC that can be combined, along with non-deacylated DHA PC, with plasma for further circulation. The second deacylation/reacylation cycle of high density lipoprotein 2-DHA PC species occurs in the liver, followed by formation of 2-DHA lysoPC in the BBB [Chen and Subbaiah, Phospholipid and fatty acid specificity of endothelial lipase: potential role of the enzyme in the delivery of docosahexaenoic Acid (DHA) to tissues, Biochim. Biophys. Acta, 171, 1319 (2007); Thies et. al., Unsaturated fatty acids esterified in 2-acyl-1-lysophosphatidylcholine bound to albumin are more efficiently taken up by the young rat brain than the unesterified form, J. Neurochem. 59, 1110 (1992)].

Studies also reported an alternative pathway of 2-DHA PC synthesis mainly via the PE methylation rather than via the CDP-choline pathway in rat liver [Delong et al., Molecular distinction of phosphatidylcholine synthesis between the CDP-choline pathway and PE methylatoin pathway, J. Biol. Chem. 274, 29682 (1999)]. The biosynthesis of 2-DHA PE via the CDP-ethanolamine pathway is an important route [Tijburg et. al., Biosynthesis of phosphatidylethanolamine via the CDP-ethanolamine route is an important pathway in isolated rat hepatocytes, Biochem. Biophys. Res. Commun. 160, 1275 (1989)].

A pharmacokinetic study of PS clearly figured out in vivo metabolic fate of the exogenous PS species mixture, which include: (i) decarboxylation to phosphatidylethanolamine, and (ii) extensive hydrolytic degradation to other lipids, mainly lysophosphatidylethanolamine [Palatini, et. al., pharmacokinetic characterization of phosphatidylserine liposome in the rat, Br. J. Pharmacol. 102, 345 (1991)].

Herein, it is very important to state again that the incorporation of DHA into the brain as a function time is about 10-fold higher from enzyme-catalyzed 2-DHA lysophospholipids than from non-esterified DHA at various times of analyses [Lagarde, Docosahexaenoic acid: neutrient and precursor of bioactive lipids, Eur. J. Lipid Sci. Technol. 110, 673 (2008)], suggesting that lysophospholipids, mainly lysoPC and lysoPE, are the best DHA transporters that may easily pass across the BBB [Chen and Subbaiah, Phospholipid and fatty acid specificity of endothelial lipase: potential role of the enzyme in the delivery of docosahexaenoic acid (DHA) to tissues, Biochim. Biophys. Acta, 171, 1319 (2007)].

Design of the Brain DHA Phospholipid Transporters on the Basis of the Metabolic Mechanism of Phospholipids Based on above knowledge of in vivo and in vitro metabolic pathways of phospholipids, a series of ideal brain DHA transporters should be: highly enriched 1-acyl chains/2-DHA-containing molecular species of highly pure phospholipids, which are expected to be not only deacylated easily for the exogenous DHA phospholipid species but also reacylated readily to reform newly-made 2-DHA related phospholipids effectively in absorption step and further circulation, followed by further releasing 2-DHA lysophospholipids that can pass across the BBB easily.

A series of phospholipids based brain DHA transporters can be designed as: (i) 1-acyl chains/2-DHA phosphatidylethanolamine (PE) species, which can be deacylated easily by pancreatic and other phosphalipase $A_2$ and then reacylated readily to reform newly-made 2-DHA PE in general circulation and partial formation of 2-DHA PC in the liver, followed by further releasing endothelial lipase-catalyzed 2-DHA-lysoPC and 2-DHA lysoPE in the BBB [Kubo et. al., Preferential incorporation of docosahexaenoic acid into nonphosphorus lipids and phosphatidylethanolamine protects rats from dietary DHA-stimulated lipid peroxidation, *J. Nutr.* 130: 1749 (2000); Merkl and Lands, Metabolism of glycerolipids, *J. Biol. Chem.* 238, 905 (1963); Masuzawa, et. al., Selective acyl transfer in the reacylation of brain glycerophospholipids. Comparison of three acylation systems for 1-al-alk-1'-enylglycero-3-phosphoethanolamine, 1-acylglycero-3-phosphocholine and 1-acylglycero-3-phosphocholine in rat brain microsomes, *Biochim. Biophys. Acta,* 1005, 1 (1989); Illingworth and Portman, The uptake and metabolism of plasma lysoPC in vivo by the brain of squirrel monkeys. *Biochem. J.* 130, 557 (1972); Chen and Subbaiah, Phospholipid and fatty acid specificity of endothelial lipase: potential role of the enzyme in the delivery of docosahexaenoic acid (DHA) to tissues, *Biochim. Biophys. Acta,* 171, 1319 (2007)].

(ii) 1-acyl chains/2-DHA phosphatidyl-monomethylethanolamine (PMME) species, which can be deacylated easily by pancreatic phospholipase $A_2$ in absorption step and then reacylated readily to reform 2-DHA PMME in general circulation, followed by producing 2-DHA PC through the PE methylation in the liver and then further releasing 2-DHA lysoPC in the BBB [Delong et al., Molecular distinction of phosphatidylcholine synthesis between the CDP-choline pathway and PE methylation pathway, *J. Biol. Chem.* 274, 29682 (1999); Lagarde, Docosahexaenoic acid: neutrient and precursor of bioactive lipids, *Eur. J Lipid Sci. Technol.* 110, 673 (2008)]; and (iii) 1-acyl chains/2-DHA phosphatidylserine (PS) species, which can be converted into related 2-DHA PE species by decarboxylation in absorption step, and then present in the plasma in the form of related 2-DHA PE species, then following the PE metabolic pathways [Palatini, et. al., pharmacokinetic characterization of phosphatidylserine liposome in the rat, *Br. J. Pharmacol.* 102, 345 (1991)].

Figure 2:
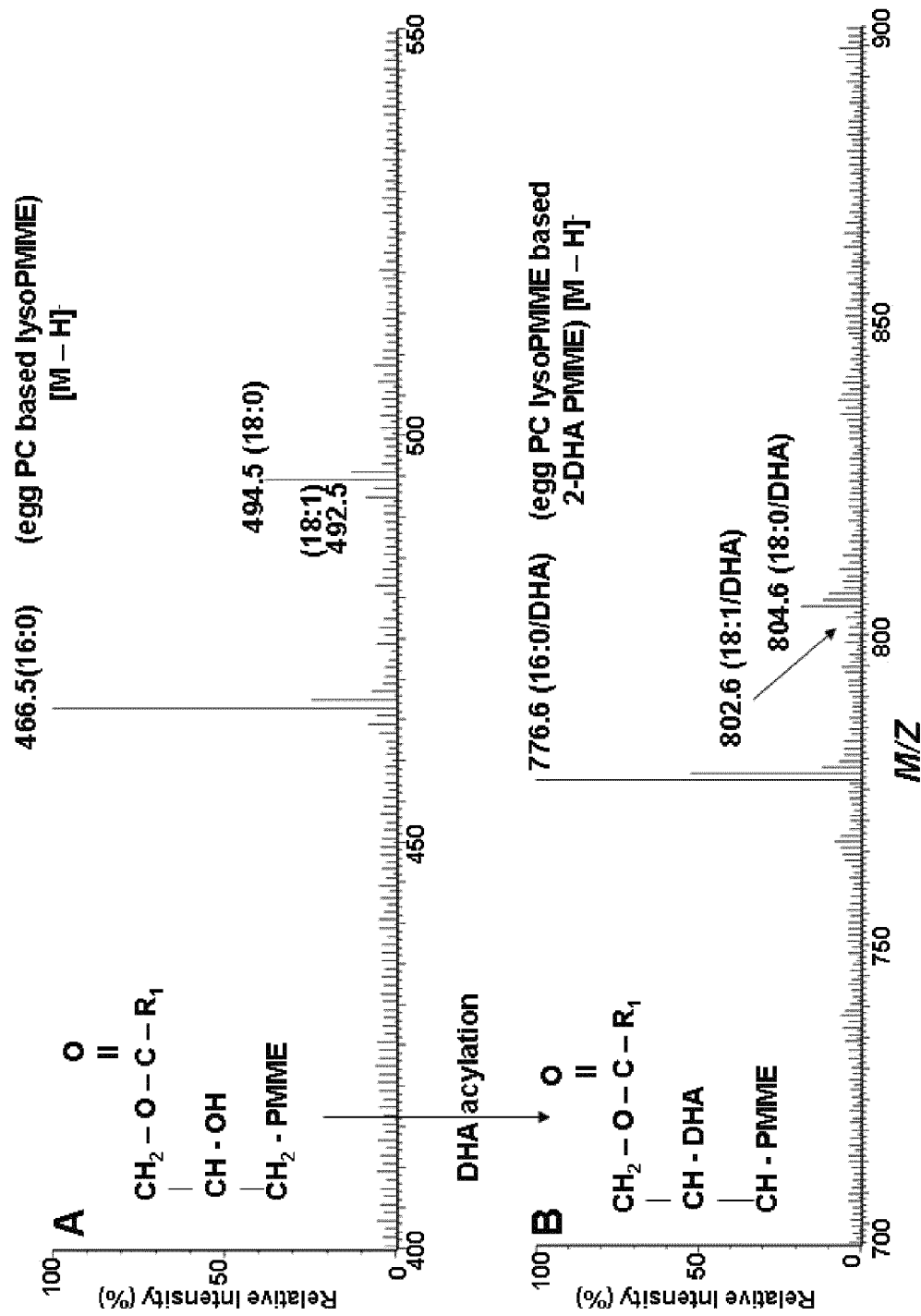
FIG. 2 shows the negative-ion electrospray mass spectra of (A) egg PC based lyso phosphatidyl-monomethylethanolamine (PMME) species that are made by phospholipase $A_2$-catalyzed transphosphatidylated egg PMME, and (B) 2-DHA PMME, made from egg PC based lysoPMME precursors.
Figure 3:
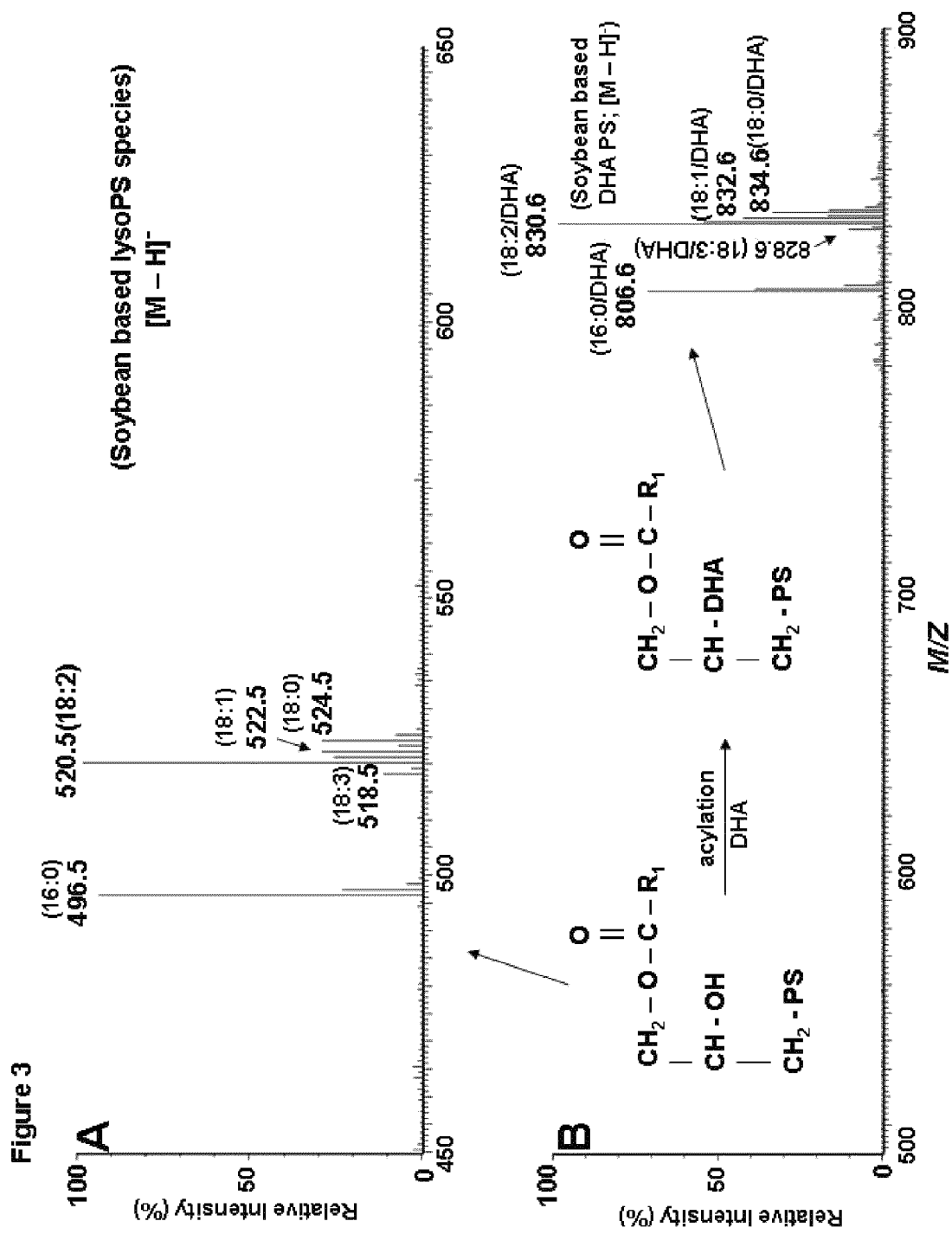
FIG. 3 shows the negative-ion electrospray mass spectra of (A) soybean based lysoPS species, and (B) 2-DHA PS, made from soybean based lysoPS precursors.

Applicants have made brain DHA transporters that include: highly pure PE, highly pure PMME and highly pure PS (over 90% of purity) that contain highly enriched 1-acyl chains/2-DHA molecular species (over 70% in the species mixture), as shown in FIG. 1 (DHA PE species), FIG. 2 (DHA PMME species) and FIG. 3 (DHA PS species), which are prepared by acylation of related lysophospholipid species with DHA.

Supporting Results Obtained from In Vitro Metabolic Experiments of the Highly Pure Phospholipids Applicants are the first to discover the methods of using highly pure 1-acyl chains/2-DHA PE species, or highly pure 1-acyl chains/2-DHA PMME species or highly pure 1-acyl chains/2-DHA PS species based brain DHA transporters to promote survival of basal forebrain cholinergic neurons in aged brain, in order to prevent and treat age-dependent basal forebrain cholinergic dysfunction related neurodegenerative disorders.

Figure 4:
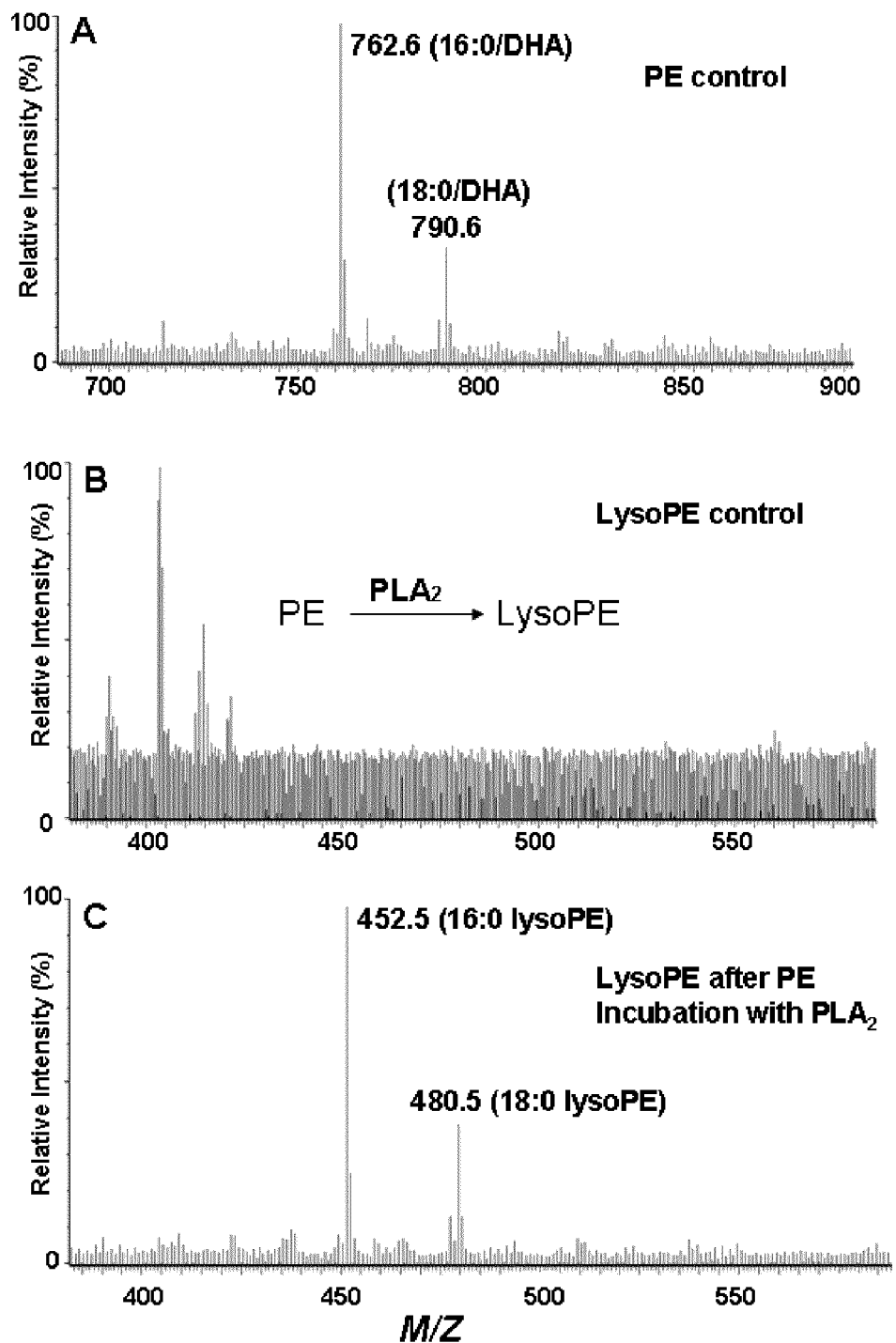
FIG. 4 shows the liquid chromatography/negative-ion electrospray mass spectra of (A) 2-DHA PE, made by egg based lysoPE precursors, and related lysoPE species before (B) and after (C) incubation of the 2-DHA PE with pancreatic phospholipase $A_2$.
Figure 5:
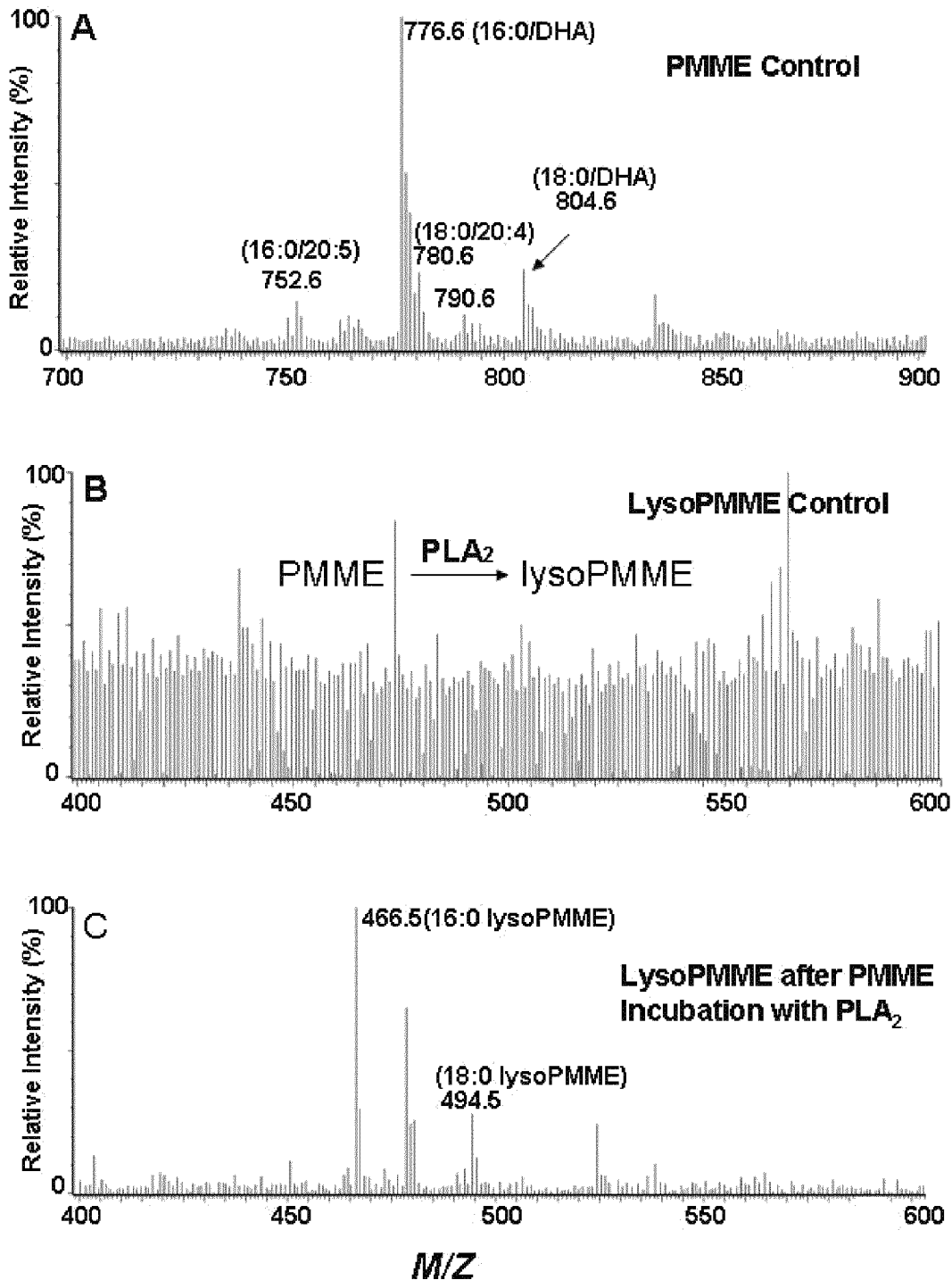
FIG. 5 shows the liquid chromatography/negative-ion electrospray mass spectra of (A) transphosphatidylated fish liver phosphatidyl-monomethylethanolamine (PMME), and lysoPMME species after incubation of the PMME without pancreatic phospholipase $A_2$(B) and with the phospholipase $A_2$(C)

Based on the metabolic pathway of phospholipids, applicants have found supporting data from in vitro metabolic experiments that highly enriched 1-acyl fatty chains/2-DHA species of both highly pure PE and highly pure PMME are good substrates for pancreatic phospholipase $A_2$, evidence by effectively releasing related lysoPE and lysoPMME species present at m/z 452 (lysoPE 16:0) and 480 (lysoPE 18:0), as well as at m/z 466 (lysoPMME 16:0) and 494 (lysoPMME 18:0), after incubation of egg yolk based DHA PE (at m/z 762 due to 16:0/DHA and 790 due to 18:0/DHA) and egg yolk based DHA PMME at m/z 776 (16:0/DHA) and 804 (18:0/DHA) with the enzyme, which are detected by liquid chromatography/negative-ion mass spectrometry (shown in FIG. 4 (PE to lysoPE) and FIG. 5 (PMME to lysoPMME, respectively).

Figure 6:
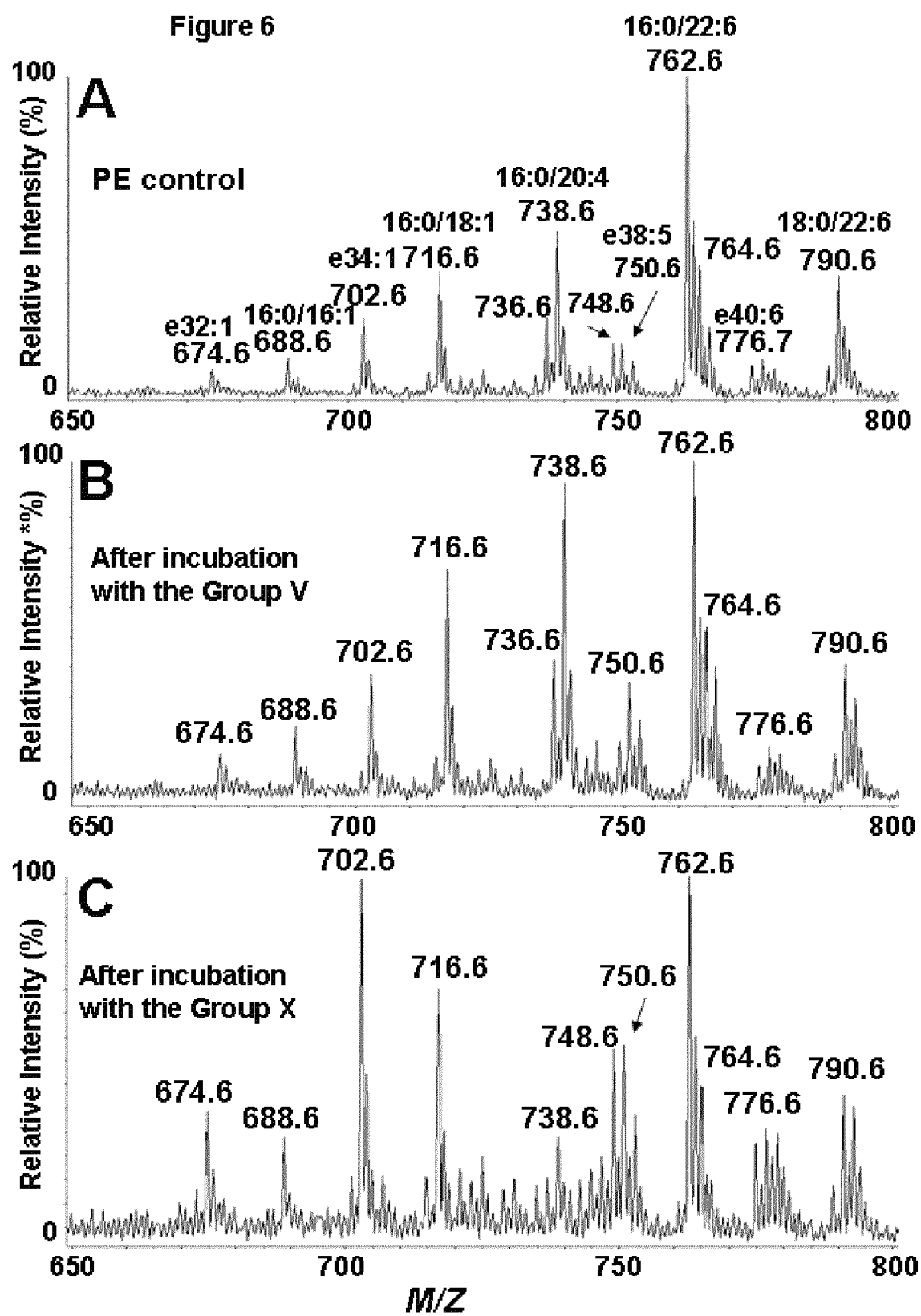
FIG. 6 shows the liquid chromatography/negative-ion electrospray mass spectra of (A) transphosphatidylated fish liver PE (control), and after incubation of the PE with human secretory phospholipase $A_2$ Group V (B) and Group X (C).

Based on the metabolic pathway of phospholipids, applicants have found supporting data from in vitro metabolic experiments that DHA PE species (over 45%) present in a natural fish liver transphosphatidylated PE species mixture are good substrates for human secretory phospholipase $A_2$ Group V and Group X, evidence by significantly decreasing the intensity of the two DHA PE species present at m/z 762 (16:0/DHA) and 790 (18:0/DHA), after incubation of the phospholipids with the enzymes, which are analyzed by liquid chromatography/negative-ion mass spectrometry (FIG. 6). DHA PMME species (over 40%) present in a natural fish liver transphosphatidylated PMME species mixture are good substrate as well for the human secretory phospholipase $A_2$ Group V and Group X (not shown).

Figure 7:
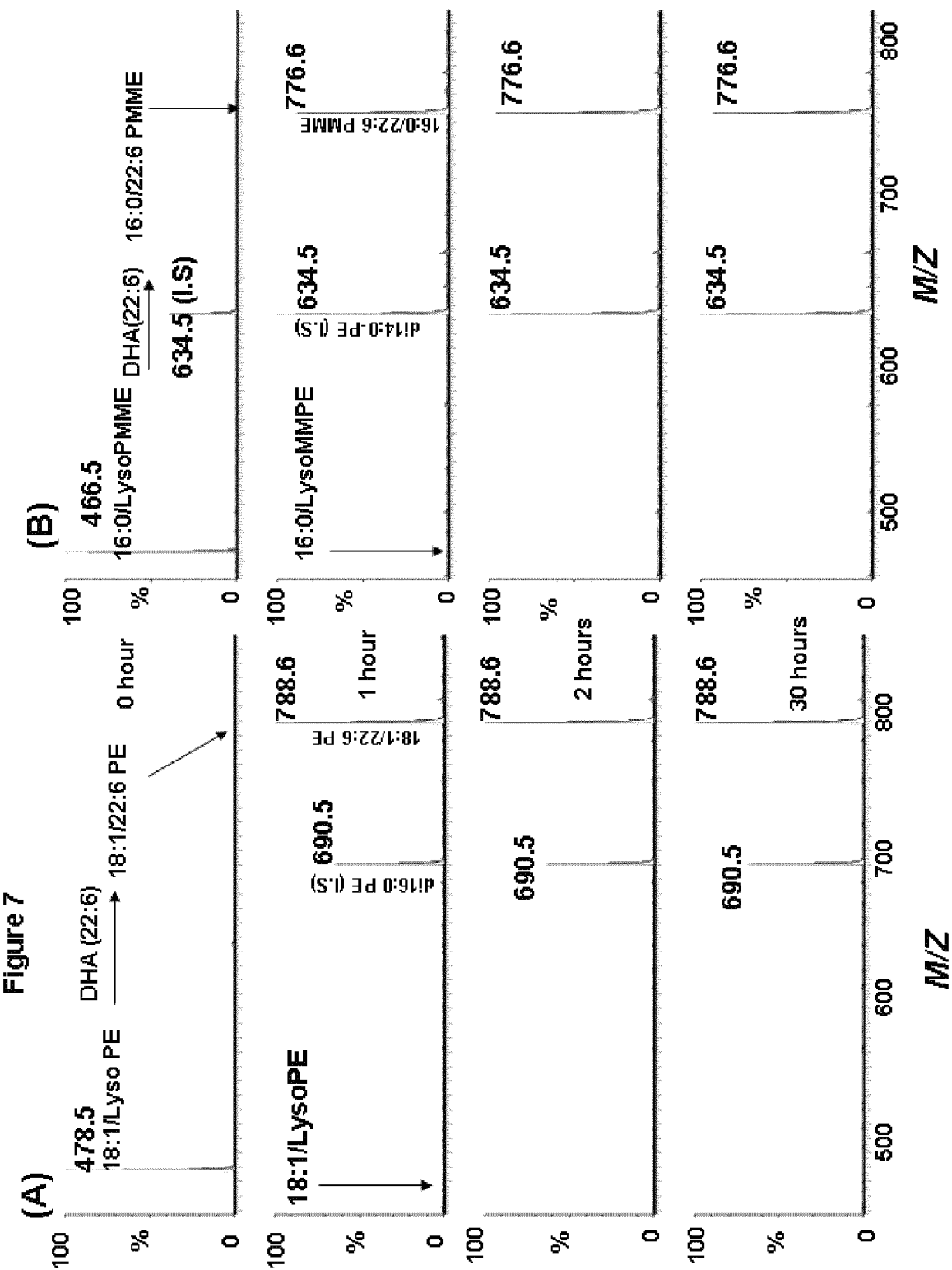
FIG. 7 shows the negative-ion electrospray mass spectra of (A) 2-DHA PE (an ion at m/z 788), made by acylation of related lysoPE (an ion at m/z 478) with DHA at the different time points (0, 1, 2 and 30 hours); and (B) 2-DHA phosphatidyl-monomethylethanolamime (PMME) (a peak at m/z 776), formed by acylation of related lysoPMME (a peak at m/z 466) with DHA at the different time point (0, 1, 2 and 30 hours), suggesting that the acylation yield of lysoPE and lysoPMME with DHA to form related DHA PE and DHA PMME species are over 95%. Ions at m/z 690 (A; 16:0/16:0 PE) and 634(B; 14:0/14:0 PE) are due to the internal standards.

Based on the metabolic pathway of phospholipids, applicants have found supporting data from in vitro metabolic experiment that yields in the acylation of lysoPE and lysoPMME species with DHA to form related 1-acyl chains/2-DHA PE species and 1-acyl chains/2-DHA PMME species are over 95% (FIG. 7A (lysoPE to PE) and 7B (lysoPMME to PMME), which are detected by the liquid chromatography/negative-ion electrospray mass spectrometry.

It also suggests that the yields in the acylation of lyso dimethylethanolamine and lysoPC species with DHA to form DHA phosphatidyl-dimethylethanolamine (30%; FIG. 8C) and DHA PC (10%; FIG. 8E) species are relatively poor, compared with those in the acylation of lysoPE (FIGS. 8A and 8D) and lysoPMME to form DHA PE and DHA PMME species (FIG. 8B). It also explains the fact that 2-DHA PC species can be synthesized in vivo mainly via the PE methylation rather than reacylation [Delong et al., Molecular distinction of phosphatidylcholine synthesis between the CDP-choline pathway and PE methylatoin pathway, *J. Biol. Chem.* 274, 29682 (1999)].

Figure 9:
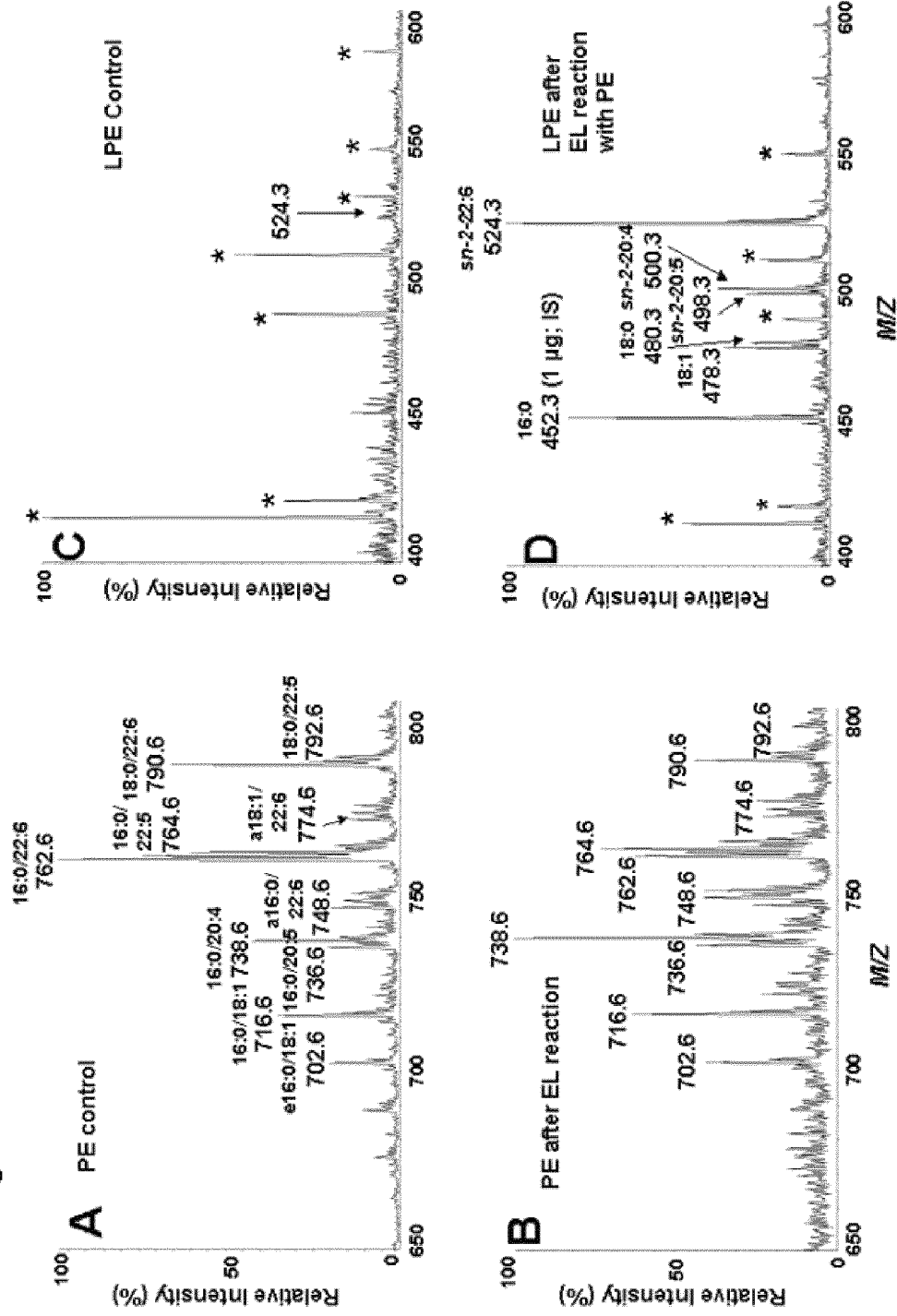
FIG. 9 shows the liquid chromatography/negative-ion electrospray mass spectra of transphosphatidylated PE species after incubation without human endothelial lipase (EL); (A) and (C), and with EL (B) and (D), suggesting that DHA PE species are good substrate for human EL, evidence by the presence of (D) 2-DHA lysoPE species (an ion at m/z 524), compared with control (C).
Figure 10:
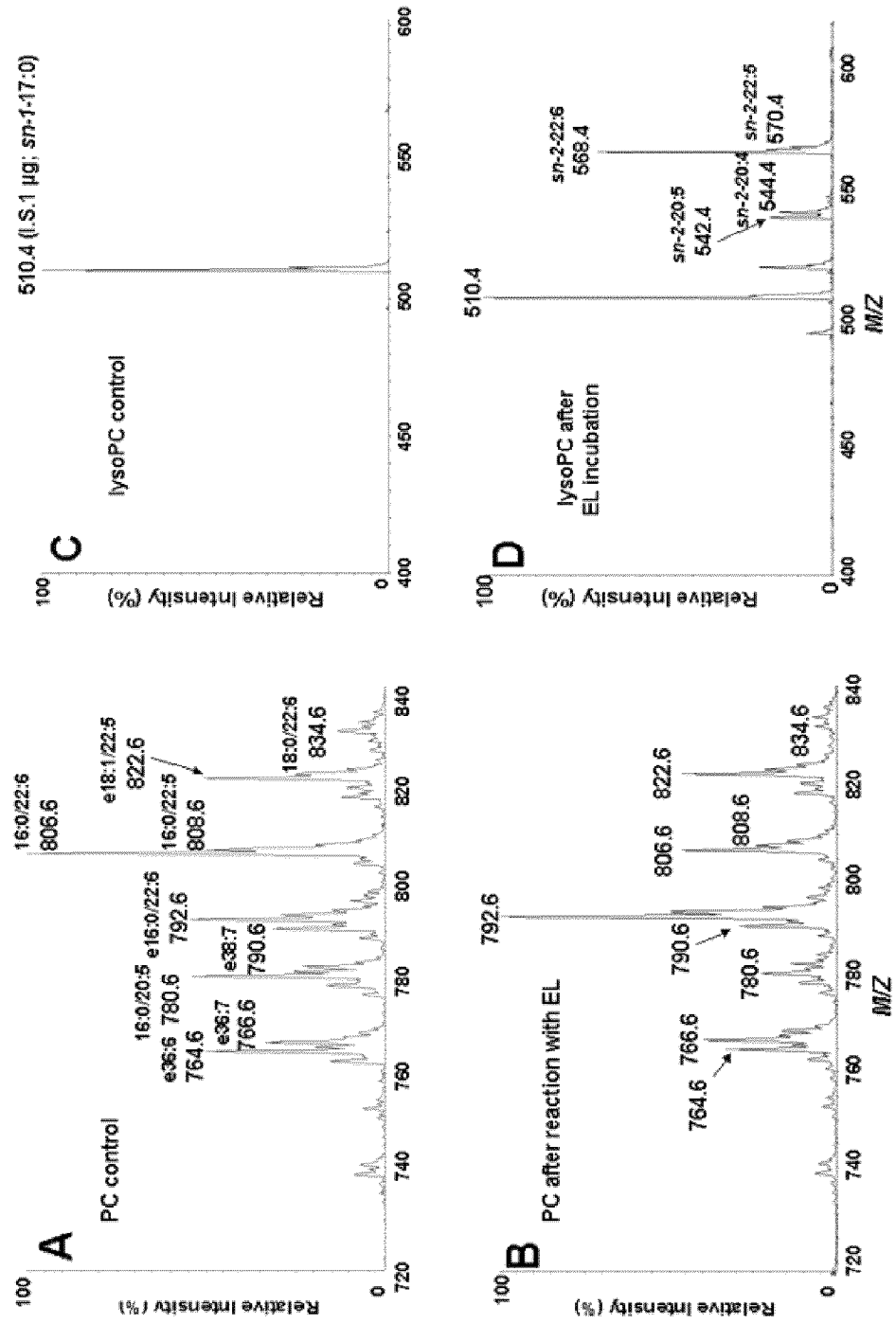
FIG. 10 shows the liquid chromatography/positive-ion electrospray mass spectra of fish liver PC species mixture after incubation without human endothelial lipase (EL) (A) and (C), and with EL (B) and (D), indicating that DHA PC species are good substrate for human EL, evidence by the presence of (D) 2-DHA lysoPC species (an ion at m/z 568), compared with control (C). DHA PC can be made from DHA PMME via the PE methylation pathway in vivo.

Based on the metabolic pathway of phospholipids, applicants have found supporting results from in vitro metabolic experiments that highly enriched 1-acyl fatty chains/2-DHA species of highly pure PE species and highly pure PC species are good substrates for human endothelial lipase, evidence by releasing related 2-DHA lysophospholipid species after incubation, detected by liquid chromatography/mass spectrometry method (FIGS. 9 and 10).

Figure 11:
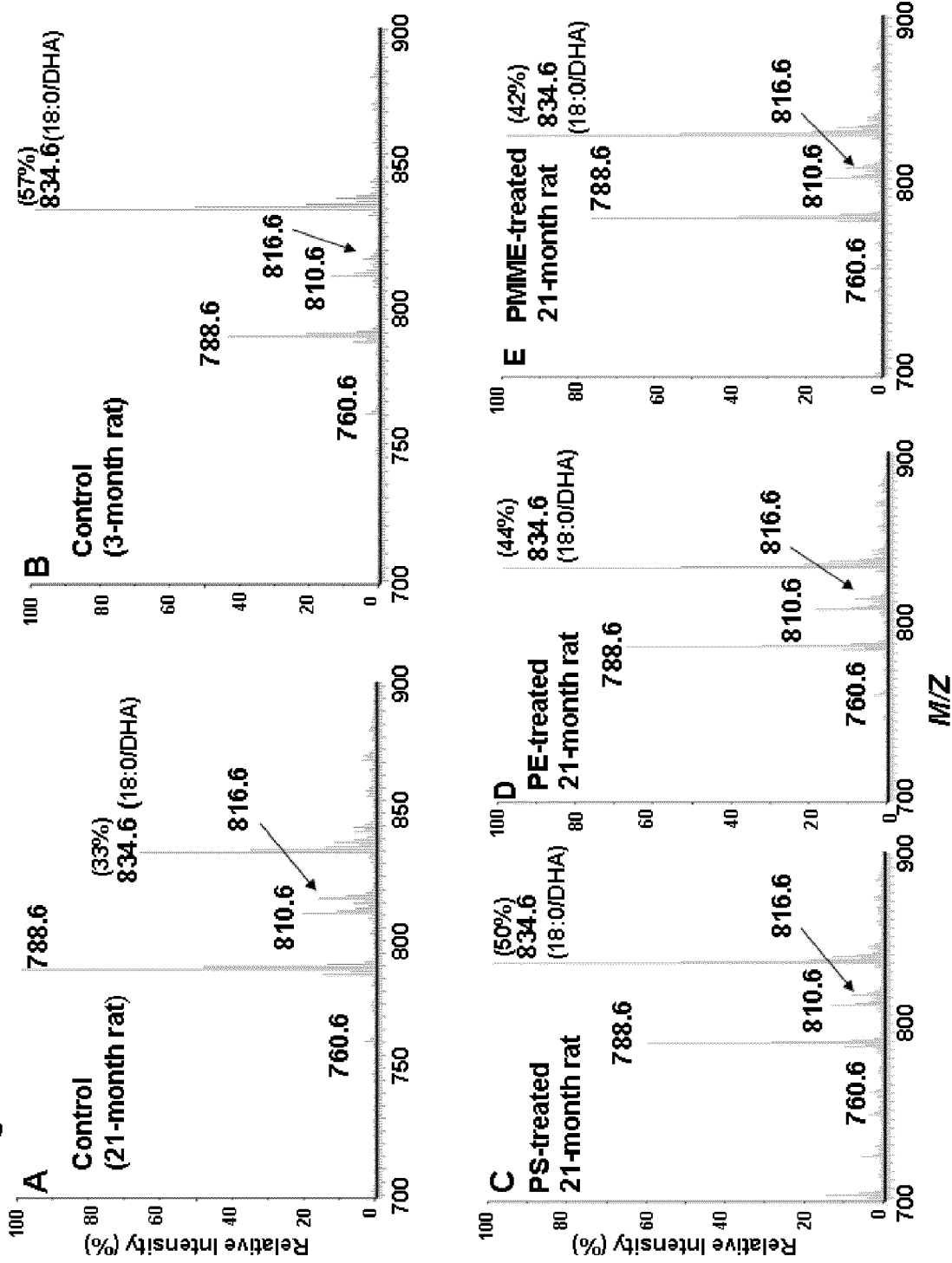
FIG. 11 shows the liquid chromatography/negative-ion electrospray mass spectra of striatal neural membrane PS molecular species of (A) 21-month old rat (first control), (C) 21-month old rat treated with DHA PS, (D) 21-month old rat treated with DHA PE, (E) 21-month old rat treated with DHA PMME, and (B) 3-month old rat (second control). It is clear to see that after treatment with the highly pure phospholipids, the percentage of 18:0/DHA PS species (m/z 834) is significantly increased, compared with the control. The spectra are obtained based on rising and falling of the negative-ion profile of the ion chromatography of both m/z 788 (18:0/18:1) and of m/z 834 (18:0/DHA).

Supporting Results Obtained from In Vivo Experiments of Highly Pure Phospholipids From in vivo experiments in 21-month old rats, applicants have found the positive benefits after using highly pure 1-acyl chains/2-DHA aminophospholipids as brain DHA transporters, evidence by observing significant reversal of abnormal percentage of neural membrane DHA PS species in the striatum of 21-month old rats after 14 days of intraperitoneal injection treatment (5 mg/kg/daily), compared with controls. FIG. 11 shows liquid chromatography/negative-ion mass spectra. An ion at m/z 834 corresponds to 1-18:0/2-DHA PS species. After the exogenous introduction of 2-DHA-PS or 2-DHA-PE or 2-DHA-PMME, abnormal percentage of 1-18:0/2-DHA PS species significantly rise to 53% (treated with PS; see Table 1 and FIG. 11C), 45% (treated with PE; Table 1 and FIG. 11D) and 45% (treated with PMME; see Table 1 and FIG. 11E), respectively, compared with controls with 35% from 21-month rat (see Table 1 and FIG. 11A) and 57% from 3-month rat (see FIG. 11B).

TABLE 1

Neural membrane PS Species (%) of aged striatum (21-month-rats) after 14 days treatment

| [M − H]⁻ | Molecular Species | Control | PS-treated | PE-treated | PMME-treated | Change (n = 5) |
|---|---|---|---|---|---|---|
| 760.6 | 16:0/18:1 | 1.36 ± 0.4 | 1.73 ± 0.6 | 1.45 ± 0.2 | 1.35 ± 0.2 | +0.1%** |
| 786.6 | 18:0/18:2 | 6.26 ± 0.3 | 4.33 ± 0.9 | 4.63 ± 0.5 | 4.84 ± 0.6 | −1.7% |
| 788.6 | 18:0/18:1 | 42.3 ± 3.7 | 29.5 ± 3.7 | 34.5 ± 7.8 | 36.8 ± 6.3 | −8.7% |
| 810.6 | 16:0/20:4 | 8.61 ± 0.4 | 7.72 ± 1.5 | 9.01 ± 1.1 | 7.13 ± 1.1 | −0.67% |
| 816.6 | 18:0/20:1 | 6.38 ± 0.3 | 3.06 ± 0.8 | 3.06 ± 0.2 | 4.17 ± 0.6 | −2.9% |
| 834.6 | 18:0/22:6 | 35.1 ± 4.6 | 53.7 ± 8.9 | 45.8 ± 5.8 | 45.6 ± 2.9 | +13% (Average) |

Figure 12:
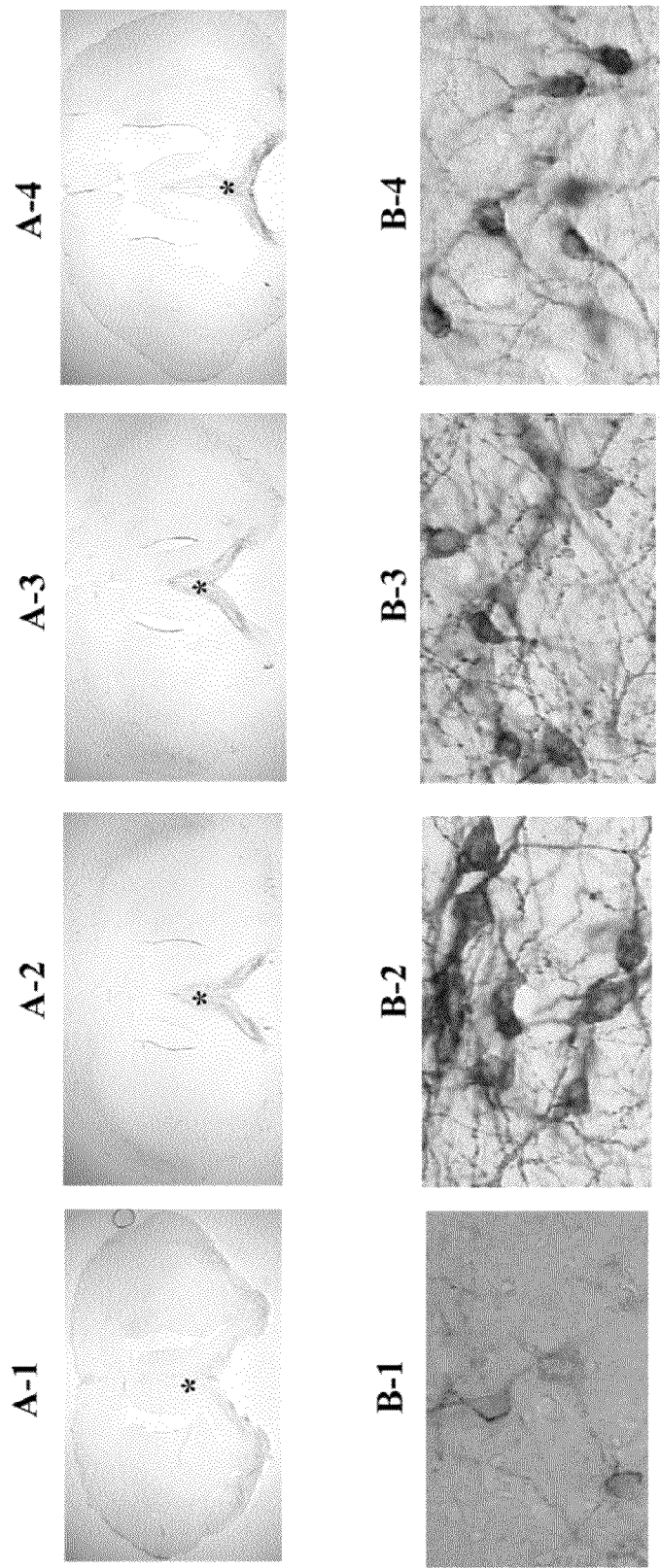
FIG. 12 shows the profile of the p-75 receptors-immunoreactive neurons in basal forebrain. A-1 (21-month rat control; treatment with saline for 14 days), A-2 (after treatment with PS, 5 mg/kg/daily of intraperitoneal injection for 14 days), A-3 (after treatment with PE; 5 mg/kg/daily of intraperitoneal injection for 14 days) and A-4 (after treatment with PMME; 5 mg/kg/daily of intraperitoneal injection 14 days) are due to the low-power photomicrography of the p75 receptor immunoreactive profiles; Related B-1 to B-4 show the high-power photomicrography of the p75 receptor-immunoreactive profiles, respectively.
Figure 13:
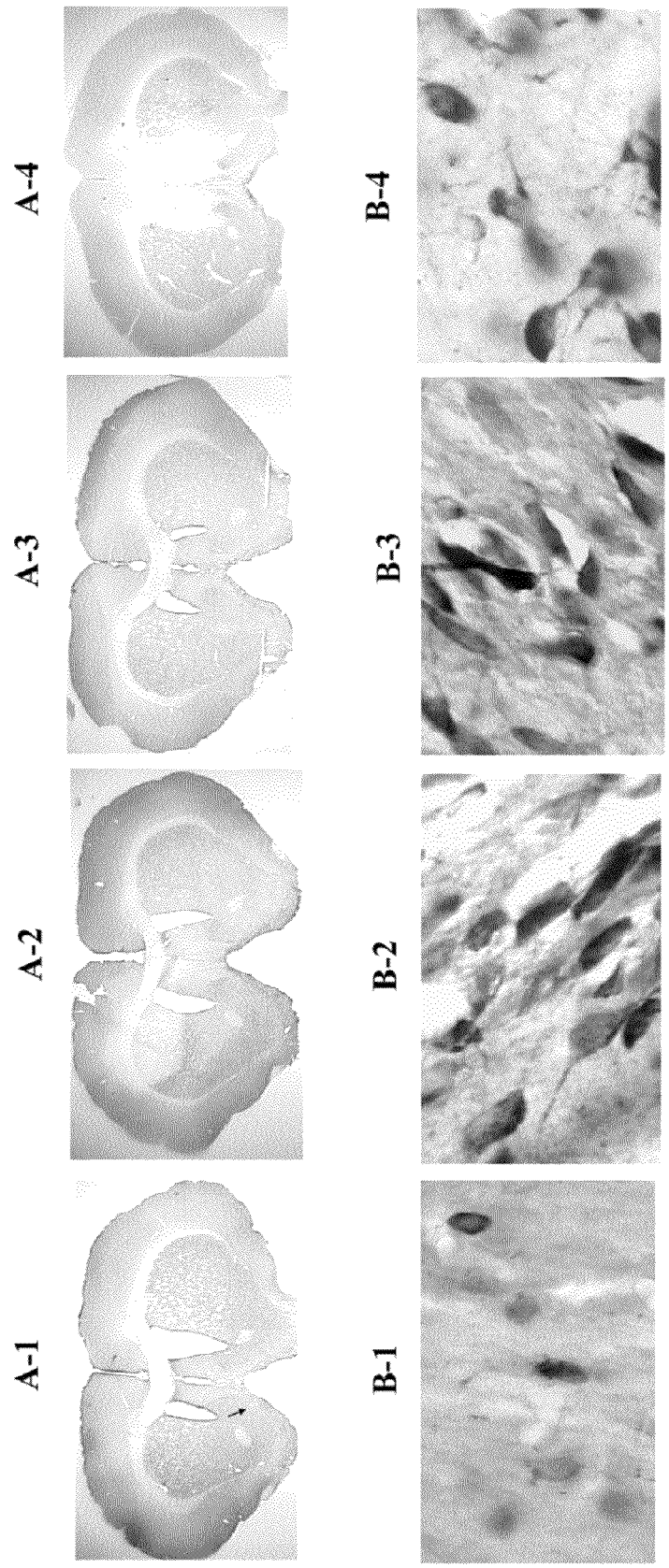
FIG. 13 shows the profile of the choline acetyltransferase-immunoreactive neurons of basal forebrain. A-1 (21-month rat control; treatment with saline for 14 days), A-2 (after treatment with PS, 5 mg/kg/daily of intraperitoneal injection for 14 days), A-3 (after treatment with PE; 5 mg/kg/daily of intraperitoneal injection for 14 days) and A-4 (after treatment with PMME; 5 mg/kg/daily of intraperitoneal injection for 14 days) are due to the low-power photomicrography of the choline acetyltransferase-immunoreactive profiles; Related B-1 to B-4 show the high-power photomicrography of choline acetyltransferase-immunoreactive profiles, respectively.

The activity recovery represented on the basis of numbers of both the p75-innunoreactive neurons (Table 2 and FIG. 12) and choline acetyltransferase (ChAT)-immunoreactive neurons (Table 3 and FIG. 13) in 21-month old rats treated with the DHA phospholipids, compared with controls (non-treated 21-month old rats), has been significantly improved after the 14 days treatment. This has been also found that the percentage of DHA plasmalogen PE species in aged striatum is significantly increased after the treatment, compared with controls (Table 4).

TABLE 2

Number of the p-75 receptor-immunoreactive neurons in 21-month rats (n = 3)

| Group | Neuron (Average) | Change (%) |
|---|---|---|
| Saline | 24804 | 0 |
| PS-treated (14 days) | 54326 | +54 ± 11* |
| PE-treated (14 days) | 42207 | +42 ± 10 |
| PMME-treated (14 days) | 44946 | +45 ± 12 |

*p < 0.05

TABLE 3

Number of the ChAT-immunoreactive neurons in 21-month rats (n = 3)

| Group | Neuron (Average) | Change (%) |
|---|---|---|
| Saline | 46414 | 0 |
| PS-treated (14 days) | 85050 | +46 ± 12* |
| PE-treated (14 days) | 71914 | +36 ± 14 |
| PMME-treated (14 days) | 63803 | +28 ± 9 |

*p < 0.05

TABLE 4

DHA PE in neural membrane of aged striatum (21-month-rats) (14 days treatment)

| [M − H]⁻ | Molecular Species | Control | PS-treated | PE-treated | PMME-treated | Change (n = 5) |
|---|---|---|---|---|---|---|
| 746.6 | a14:0/22:6 | 4.73 ± 0.7 | 7.13 ± 0.9 | 6.76 ± 0.8 | 4.50 ± 0.4 | +23%** |
| 762.6 | 16:0/22:6 | 2.40 ± 0.3 | 2.90 ± 0.5 | 2.70 ± 0.6 | 1.50 ± 0.8 | 0% |
| 772.6 | p18:1/22:6 | 3.96 ± 0.5 | 5.80 ± 0.6 | 6.70 ± 1.1 | 7.50 ± 1.0 | +41% |
| 774.6 | p18:0/22:6 | 14.2 ± 0.6 | 20.2 ± 2.9 | 19.6 ± 1.0 | 24.1 ± 1.7 | +34% |
| 790.6 | 18:0/22:6 | 10.7 ± 0.8 | 13.9 ± 1.3 | 12.6 ± 0.3 | 13.7 ± 0.7 | +20% (Average) |

The method of using highly pure PS or highly pure PE or highly pure PMME (all are over 90% of purity) that contain highly enriched 1-acyl chains/2-DHA molecular species (over 70% in the species mixtures) to promote survival of basal forebrain cholinergic neurons in aged striatum have been demonstrated, evidence by reversal of the percentage of aged striatal neural membrane DHA PS and DHA plasmalogen PE species, and by recovery of the activity of the p-75 neurotrophin receptor and choline acetyltransferase of the neurons, leading to both prevention and treatment of age-dependent basal forebrain cholinergic dysfunction related neurodegenerative disorders.

A major advantage of using the brain DHA transporters for age-dependent neurodegenerative disorders are: (1) fewer side-effects for a long term of administration, compared with use of chemically synthesized drugs; and (2) efficacy in the prevention of age-dependent neurodegenerative disorders through simultaneously delaying the underlying pathological process of neuronal apoptosis.

EXAMPLE 1

Preparation of Highly Enriched 1-acyl Chains/2-DHA Species of Highly Pure Phospholipids Preparation of Highly Enriched 1-acyl Chains/2-DHA PE Species (See the Following Chemical Structure)

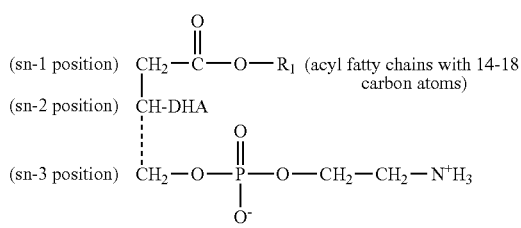

Method 1:

PE was purified from crude soybean phospholipids by silica chromatography. About 500 mg of lysoPE species mixture was obtained after $PLA_2$ treatment of about 5 grams of purified soybean PE (see FIG. 1A). A solution was made by stirring 550 mg of free DHA (BIOMOL, Plymouth Meeting, PA, USA), 350 mg of dicyclohexylcarbodiimide and 200 mg of 4-(dimethylamine) pyridine in 20 mL of chloroform for 60 min [Selinger and Lapidot, Synthesis of fatty acid anhydrides by reaction with dicyclohexylcarbodiimide, *J. Lipid Res.* 7, 174 (1966)], and then added to a container containing about 500 mg of the lysoPE species. The vial was fully filled with argon and then put into another container in which nitrogen was fully filled. It was left to react at 40° C. for 2 hours. The reaction mixture was then applied to an 800-mL silica column equilibrated with chloroform. After removing remained DHA and the chemical reagent by mixtures of chloroform/methanol (95/5 and 90/10; v/v), the 2-DHA PE species was eluted with a mixture of chloroform/methanol (80/20 (v/v)) with over 95% purity (see FIG. 1).

Method 2:

About 6 grams of silica column purified PC (from egg yolk or soybean) species were treated with transphosphatidylation, in order to make related PE species. About 500 mg of purified lysoPE species, which are obtained by PLA2-catalyzed purified PE species, were used for the preparation of highly pure 1-acyl chains/2-DHA PE as mentioned above. The products are identified by the negative-ion electrospray mass spectrometry.

Preparation of Highly Pure 1-acyl Chains/2-DHA PMME Species (See the Following Chemical Structure)

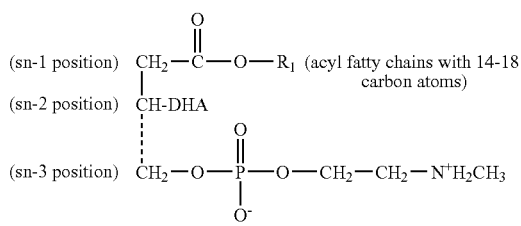

Method: About 500 mg of $PLA_2$-hydrolyzed egg yolk or soybean based lysoPMME species (FIG. 2A), which are made by transphosphatidylation of purified egg PC or soybean PC, were used for the preparation of highly pure 1-acyl chains/2-DHA PMME (FIG. 2B), as mentioned above in the preparation of related 2-DHA PE products.

Preparing Highly Enriched 1-acyl Chains/2-DHA Species of Highly Pure PS (See the Following Chemical Structure);

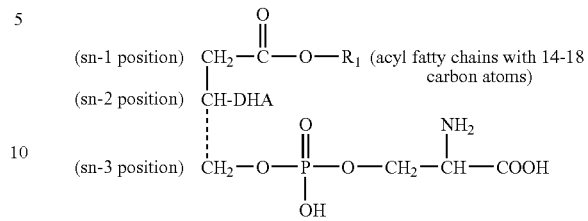

Method: About 500 mg of $PLA_2$-catalyzed lysoPS species, which is produced from transphosphatidylated PS made from purified soybean PC species, was used for the preparation of highly pure 1-acyl chains/2-DHA PS species, as mentioned above in the preparation of related 2-DHA PE products. FIG. 3 shows the negative-ion electrospray mass spectra of (A) soybean based lysoPS species and (B) 2-DHA PS species, made from the soybean based lysoPS(A).

EXAMPLE 2

In vitro Metabolic Profiles of Highly Pure Phospholipids Incubated with the Pancreatic Phospholipase $A_2$, in Order to Evaluate the Specificity of DHA Phospholipid Species for the Enzyme The experiment was done on the basis of the published method [Singh and Subbaiah, modulation of the activity and arachidonic acid selectivity of group X secretory Phospholipase $A_2$ by sphingolipids, *J. Lipid Res.* 48, 683 (2007)]. Briefly, highly pure PE was incorporated into liposome by sonication. The reaction mixture for assay of the pancreatic $PLA_2$ (2 units) contains 100 μM the DHA phospholipid, 100 mM Tris/Cl (pH 8.0), 0.1% bovine serum albumin, and 10 nM $CaCl_2$ in a final volume of 200 μl. The incubation was carried out for 30 min at 37° C. After extraction with the method of Blign and Dyer, the lipids were analyzed by the liquid chromatography/mass spectrometry. The same experiment was also done using highly pure PMME as substrate, as mentioned above. It is clear to see that the two brain DHA transporters are good substrates for the pancreatic $PLA_2$, evidence by releasing related lysophospholipid species (FIGS. 4 and 5), detected by liquid chromatography/negative-ion mass spectrometry.

EXAMPLE 3

In vitro Metabolic Profiles of Highly Pure Phospholipids Incubated with the Human Secratory Phospholipase $A_2$ Group V and Group X, in Order to Evaluate the Specificity of DHA Phospholipid Species for the Enzymes Recombinant human secretory $PLA_2$ Group V and Group X, which were used in the experiment, can be generated in the mammalian systems and act more readily on lipoproteins and cell membranes [Cho, Structure, function and regulation of Group V phospholipase $A_2$, *Biochim. Biophys. Acta.* 1488, 48 (2000)]. The specific activity of the enzymes was calculated as micrograms of fatty acid released from purified soybean PC and was corrected for the value of the control samples, in which the substrates were incubated in the absence of the two enzymes.

A substrate of PE DHA species in a natural lipid mixture used in experiment was made by transphosphatidylation of fish liver PC [Chen and Subbaiah, Phospholipid and fatty acid specificity of endothelial lipase: potential role of the enzyme in the delivery of docosahexaenoic Acid (DHA) to tissues, Biochim. Biophys. Acta, 171, 1319 (2007)]. The reason of using this substrate is that composition of the species mixtures should be closed to the expected DHA PE species present in plasma. After the incubation as mentioned above and lipid extraction, the phospholipids were analyzed by liquid chromatography/negative-ion mass spectrometry. FIG. 6 shows the liquid chromatography/negative-ion mass spectra of control sample (A), the lipids after treatment with sPLA$_2$ Group V for 30 min (B) and sPLA$_2$ Group X (C) for 30 min. It is clear to see that DHA-PE species are good substrates of the two human enzymes. The percentage of the two major DHA PE species (at m/z 762 (16:0/DHA and 790 (18:0/DHA) dropped down (see the FIG. 7 and included explanation on it) after the enzyme treatment.

The profile of transphosphatidylated DHA-MMPE species mixture after treatment with the both PLA$_2$s is similar to that of transphosphatidylated DHA-PE (not shown).

DHA-PS species are not good substrates for the two enzymes (not shown). So it is also demonstrated indirectly that DHA-PS species cannot be metabolited effectively by human enzymes, as least human sPLA$_2$ Group V and sPLA$_2$ Group X. But after decarborxylation to form PE and LysoPE in absorption steps [Palatini, et. al., pharmacokinetic characterization of phosphatidylserine liposome in the rat, Br. J. Pharmacol. 102, 345 (1991)], newly made DHA-PE species may be metabolized as the pathway of DHA-PE species.

EXAMPLE 4

Figure 8:
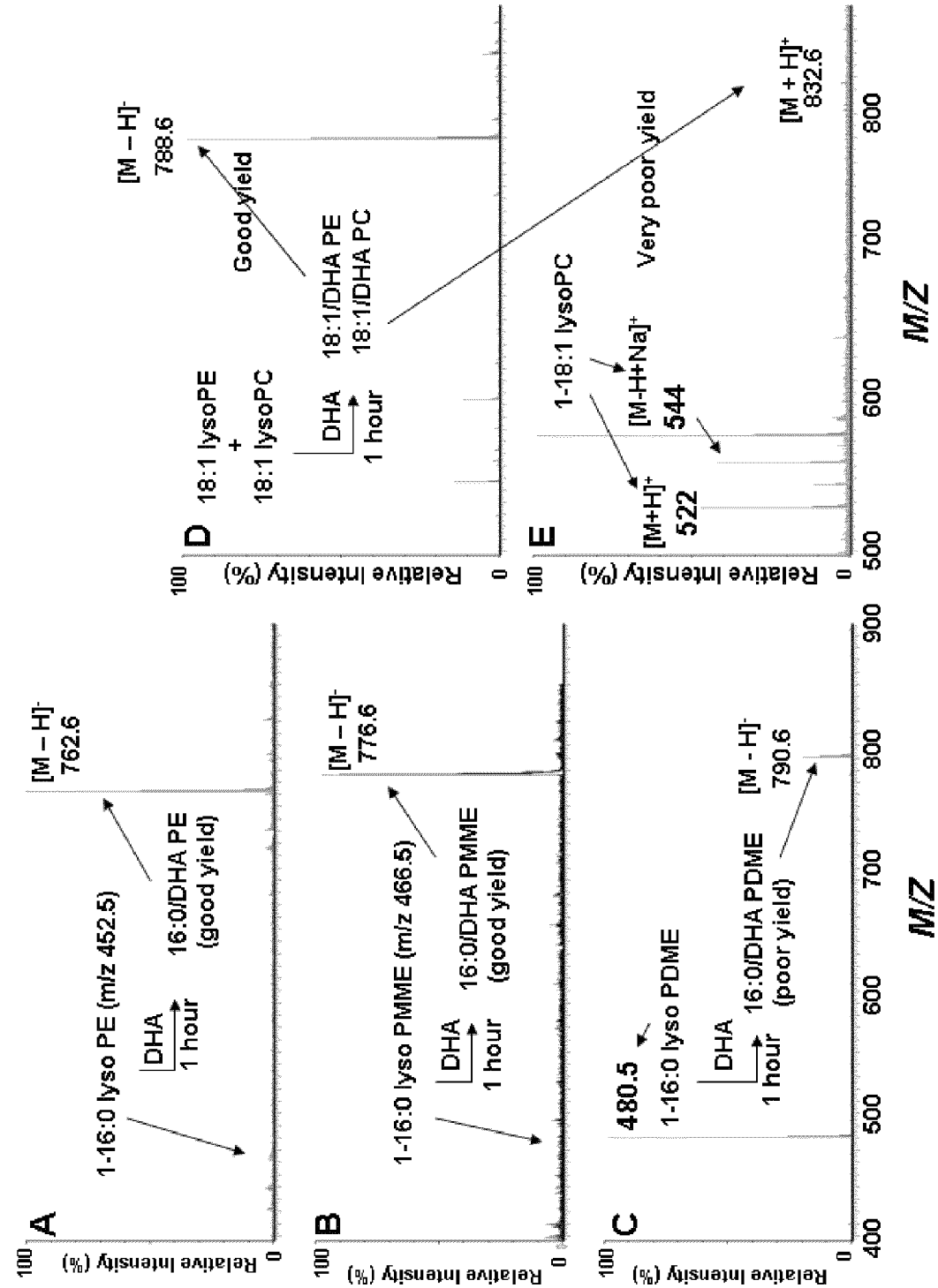
FIG. 8 shows the negative-ion and positive-ion electrospray mass spectra of (A) 2-DHA PE, acylated from related lysoPE with DHA, (B) 2-DHA PMME, formed by acylation of related lysoPMME with DHA; (C) 2-DHA phosphatidyl-dimethylethanolamine (PDME), produced by acylation of lysoPDME with DHA; and (D and E) comparison of yields of 2-DHA PC by the acylation of related lysoPC with DHA (E) and 2-DHA PE by acylation of related lysoPE with DHA (D). The results indicate that the yield for the formation of DHA PE and DHA PMME by non-enzymatic acylation of lysoPE and lysoPMME species with DHA are much higher, compared with those of the acylation of lysoPDME and lysoPC with DHA.

In vitro Experiment of Acylation of DHA Phospholipids from Related Lysophospholipids by Non-enzymatic Reaction, in Order to Roughly Evaluate the Reformation of DHA Phospholipids from Acylation of Lysophospholipids with DHA About 30 mg of a species mixture of lysoPE or lysoPMME or lyso phosphatidyl-dimethylethanolamine (lysoPDME) was mixed with a DHA solution, respectively, which was made by stirring 35 mg of free DHA, 15 mg of dicyclohexylcarbodiimide and 10 mg of 4-(dimethylanime) pyridine in 1 mL of chloroform in a vial for 60 min. The vial then was fully filled with argon and then put into another container in which nitrogen is fully filled. It is left to react at 40° C. for 1 hour. After dilution of the mixture with chloroform and methanol, the lipids in the mixture were analyzed by the negative-ion electrospray mass spectrometry (FIG. 8). It is clear to see that the yields of acylation of lysoPE (FIG. 8A) and lysoPMME (FIG. 8B) with DHA are very high (more than 95%), compared with that of lysoPDME (about 30%). The yield of acylation of a mixture of lysoPE (D) and lysoPC (E) with DHA is very different (over 95% yield for lysoPE species; less than 10% for lysoPC species), suggesting that lysoPE and lysoPMME can be reacylated readily with DHA to further form related DHA PE and DHA PMME.

EXAMPLE 5

In vitro Metabolic Profiles of the Highly Pure Phospholipids Incubated with Human Endothelial Lipase Endothelial lipase (EL) is the newest member of the lipase family that is expressed in several tissues including brain. It is unique among the lipases in having a substrate preference predominantly for phospholipids, and in not requiring bile salts or apoproteins for its action on phospholipids. The activity of EL has been shown to be inversely correlated with high density lipoproteins (HDL) levels in the plasma, showing its role in HDL metabolism. Recombinant human endothelial lipase was used in the experiment. The specific activity of the enzyme used in the experiment was 520 nmol fatty acid released/hour/ml of medium, using 16:0-16:0 PE.

Transphosphatidylated fish liver PE species were used as substrates in the experiment [Chen and Subbaiah, Phospholipid and fatty acid specificity of endothelial lipase: potential role of the enzyme in the delivery of docosahexaenoic Acid (DHA) to tissues, Biochim. Biophys. Acta, 171:1319 (2007)]. FIG. 9 shows the negative-ion electrospray mass spectra of control sample (A and C), and the DHA species after treatment of the PE with EL for 30 min (B and D). It is seen clearly that DHA-PE species are good substrates for the human EL since the percentage of the two DHA PE species 16:0/DHA at m/z 762 and 18:0/DHA at m/z 790 are down, respectively, evidence by the presence of DHA lysoPE species at m/z 524 (FIG. 9D).

FIG. 10 shows the positive-ion electrospray mass spectra of control sample (A and C), and the DHA species after treatment of fish liver PC with EL for 30 min (B and D). It is clear to see that DHA PC species are good substrates for the human EL as well. After the incubation, the percentage of the two DHA PC species 16:0/DHA at m/z 806 and 18:0/DHA at m/z 834 are down, respectively, evidence by the presence of DHA lysoPC species at m/z 568 (FIG. 10D).

DHA-PS species are not good substrates for the human EL. After decarborxylation to form PE in the absorption step [Palatini, et. al., pharmacokinetic characterization of phosphatidylserine liposome in the rat, Br. J. Pharmacol. 102; 345 (1991)], derived-DHA PE species are metabolized as the pathway of DHA-PE species.

EXAMPLE 6

In vivo Profiles of Neural Membrane DHA PS in Aged Striatum Before and After Intraperitoneal Treatment with the Highly Pure Phospholipids Animal experiments: 21-month old rats (Sprague-Dawley rats; weighted from 200-300 g; 4 rats for controls; 15 rats used for the treatment (5 rats for each group); 3-month young rats (3 rats)) were used in the study. Saline as well as highly pure DHA PS, highly pure DHA PE and highly pure DHA PMME were applied for the intrapreritoneal treatment with 5 mg/kg/daily dosage for 14 days.

After that, a small part of the striatum of the rats was collected, and the lipids in the tissues were extracted by the method of Bligh/Dyes and then analyzed by the liquid chromatography/negative-ion electrospray mass spectrometry. The intensities of the ions were used to calculate the percentage of each PS species in the species mixture (See Table 1 in details).

EXAMPLE 7

In vivo Profiles of p75 Neurotrophin Receptor- and Choline Acetyltransforase-immunoreactive Neurons Before and after Intraperitoneal Treatment with the Highly Pure Phospholipids Profiles (numbers) of the p75 neurotrophin receptor- and choline acetyltransferase-immunoreactive neurons before and after treatment were obtained based on the published methods [Mufson, et al., Loss of basal forebrain P75$^{NTR}$ immunoreactivity in subjects with mild cognitive impairment and Alzheimer's disease. *J. Comparative Neurology* 443, 136 (2002); Dowd, et. al., Targeted disruption of the galanin gene reduces the number of basal forebrain cholinergic neurons and impairs learning and long-term potential in an age-dependent manner. *Proc. Natl. Acad. Sci.* 97, 11569 (2000)].

Briefly, after picking up a small part of the striatum, the brain samples were injected with an overdose of pentobarbital (40 mg/kg), and followed by treatment with 300 ml of 4% paraformaldehyde in phosphate buffer (pH 7.4), and cryoprotected in 30% sucrose in phosphate buffer at 4° C. Then the brain was cut in frozen at 40 µm thickness with a sliding knife microtome using a uniform and systematic procedure for all cases. The tissue sections were stored at −20° C. for the further use.

The immunohistochemical procedure for the p75 receptor and choline acetyltransforase (ChAT) was continued by using the labeled antibody in which sections was sequentially incubated in the biotinylated goat anti-rabbit IgG (Vector labs. Burlingame, Calif.; 1:200) and then the "Elite" avidin-biotin complex (ABC Kits, Vector labs; 1:500) was separated by washes in a Triton-buffered saline solution containing 0.05% Triton X-100.

Quantitative assessment: the computerized optical dissector system was consisted of a computer assisted image analysis, a microscope, a computer-controlled x-y-z motorized stage, a stereological software program and a high-sensitivity video camera. Prior to the measurements, the instrumentation was calibrated. The average tissue thickness of the sections and the antibody penetration throughout the whole tissue section was measured by dissectors using imaging capture technique. The numbers of the p75 receptor- and choline acetyltransferase-immunoreactive neurons (N) was calculated using the following formula: $N=N_V \cdot V$; $N_V$ is the numerical density, and V is the volume of the p75 receptor or choline acetyltransferase as determined by the Cavarlier's principle.

Statistical analyses: a person blinded to the bio-product treatment and lesion condition will perform all analyses. A repeated measure ANOVA was performed to discern group differences over time.

The molecular species analyses of the phospholipids by liquid chromatography/negative-ion and positive-ion electrospray mass spectrometry were performed on a Micromass Platform LC/MS (Waters, Mass., USA). Normal-phase HPLC was performed with a 3-µm Spherisorb silica column (2.0×150 mm; Waters, Mass.), which was eluted with a linear gradient of 100% solvent A (chloroform/methanol/30% ammonium hydroxide, 80:19.5:0.5, by vol) to 100% solvent B (chloroform/methanol/water/30% ammonium hydroxide, 60:34.5:5:0.5, by vol) for 15 min, then in 100% solvent B for 10 min. 20 µl of the lipids in methanol/chloroform (2:1, by vol) were injected into the liquid chromatography/mass spectrometry system. The flow rate was 350 µl/min.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. A method of treating age-dependent basal forebrain cholinergic dysfunction related neurodegenerative disorders, consisting essentially of: administering to a patient in need thereof a composition consisting essentially of a lipid composition comprising a therapeutically effective amount of highly enriched 1-acyl chains/2-docosahexaenoic acid containing molecular species of highly pure phospholipids to promote survival of aged basal forebrain cholinergic neurons, the phospholipids selected from the group consisting of phosphatidylserine, phosphatidylethanolamine, and phosphatidyl-monomethylethanolamine wherein said highly enriched 1-acyl chains/2-docosahexaenoic acid containing molecular species of highly pure phospholipids are over 70% of the lipid composition.

2. The method of claim 1, wherein the said highly pure phospholipids are over 90% pure by weight.

3. The method of claim 1, wherein the said 1-acyl chains are the mixture of acyl fatty groups of 14 to 18 carbon atoms.

4. The method of claim 1, wherein the said a therapeutically effective amount ranges from about 100 to about 600 milligrams per daily dosage.

5. The method of claim 1, wherein the said age-dependent basal forebrain cholinergic dysfunction related neurodegenerative disorders are selected from the group consisting of dementia, cognitive deficits, and Alzheimer's disease.

* * * * *